(12) United States Patent
Heo et al.

(10) Patent No.: US 12,139,519 B2
(45) Date of Patent: Nov. 12, 2024

(54) CRY2 VARIANT HAVING INCREASED PHOTOSENSITIVITY AND USE THEREOF

(71) Applicant: INSTITUTE FOR BASIC SCIENCE, Daejeon (KR)

(72) Inventors: Wondo Heo, Daejeon (KR); Sungsoo Kim, Jinju-si (KR); Sang Kyu Lee, Seoul (KR); Taeyoon Kyung, Incheon (KR)

(73) Assignee: INSTITUTE FOR BASIC SCIENCE, Daejeon (KR)

( * ) Notice: Subject to any disclaimer, the term of this patent is extended or adjusted under 35 U.S.C. 154(b) by 780 days.

(21) Appl. No.: 17/293,568

(22) PCT Filed: Nov. 13, 2019

(86) PCT No.: PCT/KR2019/015459
§ 371 (c)(1),
(2) Date: May 13, 2021

(87) PCT Pub. No.: WO2020/101355
PCT Pub. Date: May 22, 2020

(65) Prior Publication Data
US 2022/0002362 A1    Jan. 6, 2022

(30) Foreign Application Priority Data
Nov. 13, 2018    (KR) .......... 10-2018-0139283

(51) Int. Cl.
*C07K 14/47*    (2006.01)
*C07K 14/705*    (2006.01)
*C12N 15/86*    (2006.01)

(52) U.S. Cl.
CPC ........ *C07K 14/4703* (2013.01); *C07K 14/705* (2013.01); *C12N 15/86* (2013.01); *C12N 2800/107* (2013.01)

(58) Field of Classification Search
CPC .. C07K 14/4703; C07K 14/705; C12N 15/86; C12N 2800/107
See application file for complete search history.

(56) References Cited

FOREIGN PATENT DOCUMENTS

| KR | 10-2014-0031484 | 3/2014 |
| KR | 20190000080 | 1/2019 |
| WO | 2017177017 | 10/2017 |

OTHER PUBLICATIONS

KIPO, PCT Search Report & Written Opinion of PCT/KR2019/015459 dated Mar. 5, 2020.
Taeyoon Kyung et al., "Optogenetic control of endogenous Ca2+ channels in vivo", Nat Biotechnol. Oct. 2015;33(10):1092-6. doi: 10.1038/nbt.3350. Epub Sep. 14, 2015.

(Continued)

*Primary Examiner* — Evelyn Y Pyla
*Assistant Examiner* — Katherine R Small
(74) *Attorney, Agent, or Firm* — LEX IP MEISTER, PLLC

(57) ABSTRACT

Provided is a CRY2 variant in which E279 and/or E281 having a negative charge in a $N_{277}SEGE_{281}$ sequence of SEQ ID NO: 1 is substituted with any one selected from the neutral amino acid group of alanine (A), isoleucine (I), leucine (L), valine (V), phenylalanine (F), methionine (M) and tryptophan (W), or in which S278 or G280 of a $N_{277}SEGE_{281}$ sequence of SEQ ID NO: 1 is substituted with any one selected from the bulky amino acid group of tryptophan (W) and phenylalanine (F).

14 Claims, 16 Drawing Sheets
Specification includes a Sequence Listing.

```
--1 MKMDKKTIVW FRRDLRIEDN PALAAAAHEG SVFPVFIWCP EEEGQFYPGR ASRWWMKQSL
-61 AHLSQSLKAL GSDLTLIKTH NTISAILDCI RVTGATKVVF NHLYDPVSLV RDHTVKEKLV
121 ERGISVQSYN GDLLYEPWEI YCEKGKPFTS FNSYWKKCLD MSIESVMLPP PWRLMPITAA
181 AEAIWACSIE ELGLENEAEK PSNALLTRAW SPGWSNADKL LNEFIEKQLI DYAKNSKKVV
241 GNSTSLLSPY LHFGEISVRH VFQCARMKQI IWARDKNSEG EESADLFLRG IGLREYSRYI
301 CFNFPFTHEQ SLLSHLRFFP WDADVDKFKA WRQGRTGYPL VDAGMRELWA TGWMHNRIRV
361 IVSSFAVKFL LLPWKWGMKY FWDTLLDADL ECDILGWQYI SGSIPDGHEL DRLDNPALQG
421 AKYDPEGEYI RQWLPELARL PTEWIHHPWD APLTVLKASG VELGTNYAKP IVDIDTAREL
481 LAKAISRTRE AQIMIGAA
```

(56) References Cited

OTHER PUBLICATIONS

Daphne L. Che et al., "The Dual Characteristics of Light-Induced Cryptochrome 2, Homo-oligomerization and Heterodimerization, for Optogenetic Manipulation in Mammalian Cells", ACS Synth Biol. Oct. 16, 2015; 4(10):1124-1135. doi:10.1021/acssynbio.5b00048.

Amir Taslimi et al., "An optimized optogenetic clustering tool for probing protein interaction and function", Nat Commun. Sep. 18, 2014;5:4925. doi: 10.1038/ncomms5925.

Gopal P. Pathak et al., "Benchmarking of Optical Dimerizer Systems", ACS Synth. Biol. 2014, 3, 11, 832-838, Oct. 28, 2014.

Mayssam H Ali et al., "Protein oligomerization: how and why", Bioorg Med Chem. Sep. 1, 2005;13(17):5013-20. doi: 10.1016/j.bmc.2005.05.037.

Kosuke Hashimoto et al., "Caught in self-interaction: evolutionary and functional mechanisms of protein homooligomerization", Phys Biol. Jun. 2011;8(3):035007. doi: 10.1088/1478-3975/8/3/035007. Epub May 13, 2011.

Adrian Fegan et al., "Chemically Controlled Protein Assembly: Techniques and Applications", Chem. Rev. 2010, 110, 3315-3336, Mar. 30, 2010.

Lukasz J Bugaj et al., "Optogenetic protein clustering and signaling activation in mammalian cells", Nat Methods. Mar. 2013;10(3):249-52. doi: 10.1038/nmeth.2360. Epub Feb. 3, 2013.

Ki-Young Chang et al., "Light-inducible receptor tyrosine kinases that regulate neurotrophin signalling", Nat Commun. Jun. 4, 2014;5:4057. doi: 10.1038/ncomms5057.

Nury Kim et al., "Spatiotemporal Control of Fibroblast Growth Factor Receptor Signals by Blue Light", Chemistry & Biology, vol. 21, Issue 7, Jul. 17, 2014, pp. 903-912.

Mai Khanh Nguyen et al., "Optogenetic oligomerization of Rab GTPases regulates intracellular membrane trafficking", Nature Chemical Biology vol. 12, pp. 431-436 (2016), Apr. 11, 2016.

Sangkyu Lee et al., "Reversible protein inactivation by optogenetic trapping in cells", Nature Methods vol. 11, pp. 633-636 (2014), May 4, 2014.

Daphne L. Che et al., "The Dual Characteristics of Light-Induced Cryptochrome 2, Homooligomerization and Heterodimerization, for Optogenetic Manipulation in Mammalian Cells", ACS Synth. Biol. 2015, 4, 10, 1124-1135, May 18, 2015.

Jonathan Soboloff et al., "STIM proteins: dynamic calcium signal transducers", Nat Rev Mol Cell Biol. Sep. 2012; 13(9):549-65. doi: 10.1038/nrm3414.

Xue Yang et al., "Structural and mechanistic insights into the activation of Stromal interaction molecule 1 (STIM1)", PNAS, Apr. 10, 2012,109 (15) 5657-5662; https://doi.org/10.1073/pnas.1118947109.

FIG. 1

```
  -1 MKMDKKTIVW FRRDLRIEDN PALAAAAHEG SVFPVFIWCP EEEGQFYPGR ASRWWMKQSL
 -61 AHLSQSLKAL GSDLTLIKTH NTISAILDCI RVTGATKVVF NHLYDPVSLV RDHTVKEKLV
 121 ERGISVQSYN GDLLYEPWEI YCEKGKPFTS FNSYWKKCLD MSIESVMLPP PWRLMPITAA
 181 AEAIWACSIE ELGLENEAEK PSNALLTRAW SPGWSNADKL LNEFIEKQLI DYAKNSKKVV
 241 GNSTSLLSPY LHFGEISVRH VFQCARMKQI IWARDKNSEG EESADLFLRG IGLREYSRYI
 301 CFNFPFTHEQ SLLSHLRFFP WDADVDKFKA WRQGRTGYPL VDAGMRELWA TGWMHNRIRV
 361 IVSSFAVKFL LLPWKWGMKY FWDTLLDADL ECDILGWQYI SGSIPDGHEL DRLDNPALQG
 421 AKYDPEGEYI RQWLPELARL PTEWIHHPWD APLTVLKASG VELGTNYAKP IVDIDTAREL
 481 LAKAISRTRE AQIMIGAA
```

FIG. 2

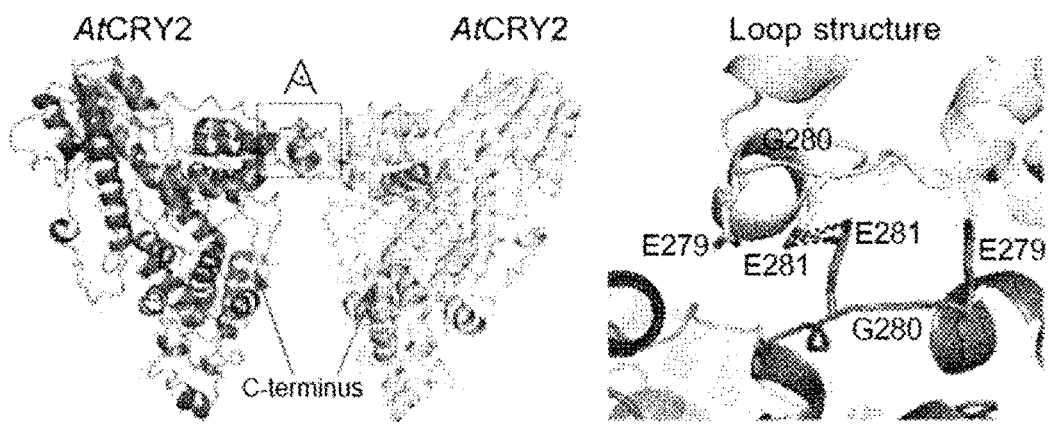

FIG. 9
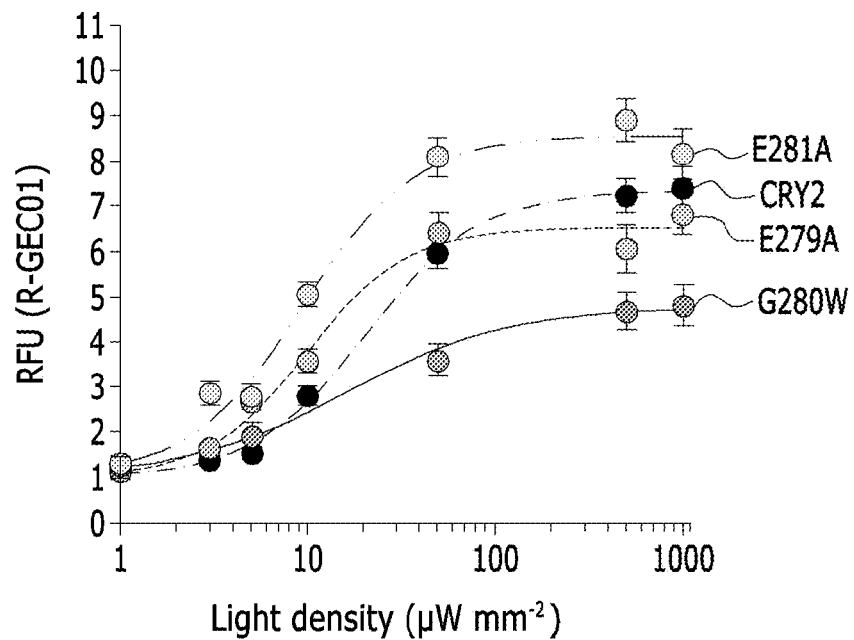
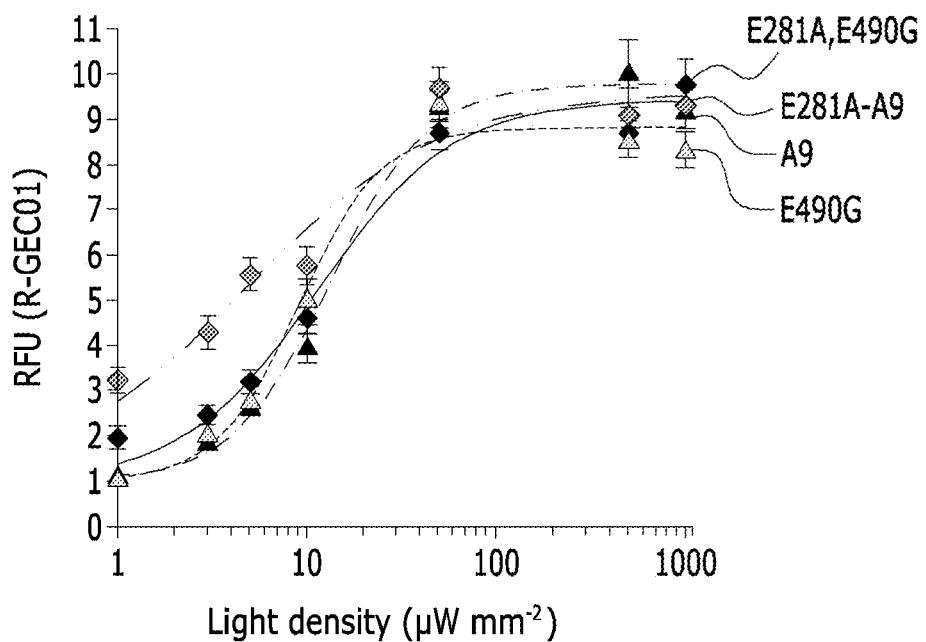

SEQUENCE LISTING

```
<160> NUMBER OF SEQ ID NOS: 24

<210> SEQ ID NO 1
<211> LENGTH: 498
<212> TYPE: PRT
<213> ORGANISM: Artificial Sequence
<220> FEATURE:
<223> OTHER INFORMATION: CRY2 of Arabidopsis thaliana

<400> SEQUENCE: 1

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
```

```
                 130                 135                 140
Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
                195                 200                 205

Ala Trp Ser Pro Gly Trp Ser Asn Ala Asp Lys Leu Leu Asn Glu Phe
210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
                260                 265                 270

Ala Arg Asp Lys Asn Ser Glu Gly Glu Glu Ser Ala Asp Leu Phe Leu
                275                 280                 285

Arg Gly Ile Gly Leu Arg Glu Tyr Ser Arg Tyr Ile Cys Phe Asn Phe
                290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
                340                 345                 350

Trp Met His Asn Arg Ile Arg Val Ile Val Ser Ser Phe Ala Val Lys
                355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
                435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala

<210> SEQ ID NO 2
<211> LENGTH: 9
<212> TYPE: PRT
<213> ORGANISM: Artificial Sequence
<220> FEATURE:
<223> OTHER INFORMATION: Additional Inserted Peptide

<400> SEQUENCE: 2
```

Ala Arg Asp Pro Pro Asp Leu Asp Asn
1               5

<210> SEQ ID NO 3
<211> LENGTH: 9
<212> TYPE: PRT
<213> ORGANISM: Artificial Sequence
<220> FEATURE:
<223> OTHER INFORMATION: Additional Inserted Peptide

<400> SEQUENCE: 3

Ala Arg Asp Pro Pro Asp Ile Asp Asn
1               5

<210> SEQ ID NO 4
<211> LENGTH: 9
<212> TYPE: PRT
<213> ORGANISM: Artificial Sequence
<220> FEATURE:
<223> OTHER INFORMATION: Additional Inserted Peptide

<400> SEQUENCE: 4

Ala Arg Asp Pro Pro Asp Ala Asp Asn
1               5

<210> SEQ ID NO 5
<211> LENGTH: 9
<212> TYPE: PRT
<213> ORGANISM: Artificial Sequence
<220> FEATURE:
<223> OTHER INFORMATION: Additional Inserted Peptide

<400> SEQUENCE: 5

Ala Arg Asp Pro Pro Asp Lys Asp Asn
1               5

<210> SEQ ID NO 6
<211> LENGTH: 9
<212> TYPE: PRT
<213> ORGANISM: Artificial Sequence
<220> FEATURE:
<223> OTHER INFORMATION: Additional Inserted Peptide

<400> SEQUENCE: 6

Ala Arg Asp Pro Pro Asp Asp Asp Asn
1               5

<210> SEQ ID NO 7
<211> LENGTH: 8
<212> TYPE: PRT
<213> ORGANISM: Artificial Sequence
<220> FEATURE:
<223> OTHER INFORMATION: Additional Inserted Peptide

<400> SEQUENCE: 7

Ala Arg Asp Pro Asp Leu Asp Asn
1               5

<210> SEQ ID NO 8
<211> LENGTH: 8
<212> TYPE: PRT
<213> ORGANISM: Artificial Sequence
<220> FEATURE:
<223> OTHER INFORMATION: Additional Inserted Peptide

<400> SEQUENCE: 8

```
Ala Arg Asp Pro Asp Ile Asp Asn
1               5

<210> SEQ ID NO 9
<211> LENGTH: 8
<212> TYPE: PRT
<213> ORGANISM: Artificial Sequence
<220> FEATURE:
<223> OTHER INFORMATION: Additional Inserted Peptide

<400> SEQUENCE: 9

Ala Arg Asp Pro Asp Ala Asp Asn
1               5

<210> SEQ ID NO 10
<211> LENGTH: 8
<212> TYPE: PRT
<213> ORGANISM: Artificial Sequence
<220> FEATURE:
<223> OTHER INFORMATION: Additional Inserted Peptide

<400> SEQUENCE: 10

Ala Arg Asp Pro Asp Lys Asp Asn
1               5

<210> SEQ ID NO 11
<211> LENGTH: 8
<212> TYPE: PRT
<213> ORGANISM: Artificial Sequence
<220> FEATURE:
<223> OTHER INFORMATION: Additional Inserted Peptide

<400> SEQUENCE: 11

Ala Arg Asp Pro Asp Asp Asp Asn
1               5

<210> SEQ ID NO 12
<211> LENGTH: 7
<212> TYPE: PRT
<213> ORGANISM: Artificial Sequence
<220> FEATURE:
<223> OTHER INFORMATION: Additional Inserted Peptide

<400> SEQUENCE: 12

Ala Arg Asp Pro Pro Asp Leu
1               5

<210> SEQ ID NO 13
<211> LENGTH: 7
<212> TYPE: PRT
<213> ORGANISM: Artificial Sequence
<220> FEATURE:
<223> OTHER INFORMATION: Additional Inserted Peptide

<400> SEQUENCE: 13

Ala Arg Asp Pro Pro Asp Ile
1               5

<210> SEQ ID NO 14
<211> LENGTH: 7
<212> TYPE: PRT
<213> ORGANISM: Artificial Sequence
<220> FEATURE:
<223> OTHER INFORMATION: Additional Inserted Peptide

<400> SEQUENCE: 14

Ala Arg Asp Pro Pro Asp Ala
```

<210> SEQ ID NO 15
<211> LENGTH: 7
<212> TYPE: PRT
<213> ORGANISM: Artificial Sequence
<220> FEATURE:
<223> OTHER INFORMATION: Additional Inserted Peptide

<400> SEQUENCE: 15

Ala Arg Asp Pro Pro Asp Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Additional Inserted Peptide

<400> SEQUENCE: 16

Ala Arg Asp Pro Pro Asp Asp
1               5

<210> SEQ ID NO 17
<211> LENGTH: 39
<212> TYPE: DNA
<213> ORGANISM: Artificial Sequence
<220> FEATURE:
<223> OTHER INFORMATION: flanking primer_forward

<400> SEQUENCE: 17
gtaaccggtc atgaagatgg acaaaaagac catcgtctg                              39

<210> SEQ ID NO 18
<211> LENGTH: 41
<212> TYPE: DNA
<213> ORGANISM: Artificial Sequence
<220> FEATURE:
<223> OTHER INFORMATION: flanking primer_reverse

<400> SEQUENCE: 18
ctccgcctcc cccactgaat tcggcagcac cgatcataat c                           41

<210> SEQ ID NO 19
<211> LENGTH: 36
<212> TYPE: DNA
<213> ORGANISM: Artificial Sequence
<220> FEATURE:
<223> OTHER INFORMATION: E279A_forward

<400> SEQUENCE: 19
aacagcgccg gcgaagaaag cgccgatctg ttcctg                                 36

<210> SEQ ID NO 20
<211> LENGTH: 36
<212> TYPE: DNA
<213> ORGANISM: Artificial Sequence
<220> FEATURE:
<223> OTHER INFORMATION: E279A_reverse

<400> SEQUENCE: 20
gctttcttcg ccggcgctgt ttttatcgcg agccca                                 36

<210> SEQ ID NO 21
<211> LENGTH: 34

```
<212> TYPE: DNA
<213> ORGANISM: Artificial Sequence
<220> FEATURE:
<223> OTHER INFORMATION: G280W_forward

<400> SEQUENCE: 21
aacagcgaat gggaagaaag cgccgatctg ttcc                                    34

<210> SEQ ID NO 22
<211> LENGTH: 36
<212> TYPE: DNA
<213> ORGANISM: Artificial Sequence
<220> FEATURE:
<223> OTHER INFORMATION: G280W_reverse

<400> SEQUENCE: 22
gctttcttcc cattcgctgt ttttatcgcg agccca                                  36

<210> SEQ ID NO 23
<211> LENGTH: 30
<212> TYPE: DNA
<213> ORGANISM: Artificial Sequence
<220> FEATURE:
<223> OTHER INFORMATION: E281A_forward

<400> SEQUENCE: 23
gaaggcgccg aaagcgccga tctgttcctg                                         30

<210> SEQ ID NO 24
<211> LENGTH: 32
<212> TYPE: DNA
<213> ORGANISM: Artificial Sequence
<220> FEATURE:
<223> OTHER INFORMATION: E281A_reverse

<400> SEQUENCE: 24
gctttcggcg ccttcgctgt ttttatcgcg ag                                      32
```

CRY2 VARIANT HAVING INCREASED PHOTOSENSITIVITY AND USE THEREOF

TECHNICAL FIELD

This disclosure relates to a CRY2 variant having increased photosensitivity and a use thereof.

BACKGROUND ART

Protein dimerization is an essential molecular mechanism that regulates signaling pathway proteins such as cell membrane receptors, kinases, and transcription factors (Ali, M. H. et al., Bioorg Med Chem, Vol. 13, pp. 5013-5020, 2005; Hashimoto, K. et al., Phys Biol Vol. 8, 035007, 2011). Therefore, synthetic tools capable of controlling protein dimerization are of great value in studying various biological events. The most widely used approach to inducing protein dimerization under certain conditions is a chemically induced homo-association system (Fegan, A. et al., Chem Rev, Vol. 110, pp. 3315-3336, 2010). However, due to the disadvantages of chemical substances such as low spatiotemporal resolution and diversity, their use for studying the dynamic properties of protein activity is limited. One method to solve the above drawback is to control the dimerization of the target protein at a specific time and space through a light-induced dimerization property of CRY2. (Bugaj, L. J. et al., Nat Methods, Vol. 10, pp. 249-252, 2013; Chang, K. Y. et al., Nat Commun Vol. 5, pp. 4057, 2014; Kim, N. et al. Chem Biol, Vol. 21, pp. 903-912, 2014; Kyung, T. et al., Nat Biotechnol, Vol. 33, pp. 1092-1096, 2015; Nguyen, M. K. et al., Nat Chem Biol, Vol. 12, pp. 431-436, 2016; Taslimi, A. et al. Nat Commun, Vol. 5, pp. 4925, 2014).

However, it is known that dimerization of a wild-type CRY2 protein or a CRY2 variant known to date is possible only under limited conditions and under high light irradiation conditions (Taslimi, A. et al., Nat Commun Vol. 5, pp. 4925, 2014; Lee, S. et al., Nat Methods Vol. 11, pp. 633-636, 2014; Che, D. L. et al., ACS Synth Biol Vol. 4, pp. 1124-1135, 2015).

DISCLOSURE

Technical Problem

The present disclosure provides a CRY2 variant capable of causing a dimerization reaction even under low illumination.

The present disclosure provides a gene encoding a CRY2 variant.

The present disclosure provides an expression vector including a gene encoding a CRY2 variant.

The present disclosure provides a transfectant transfected with an expression vector including a gene encoding the CRY2 variant.

The present disclosure provides a $Ca^{2+}$ modulator that may be fused with a CRY2 variant to control the release of $Ca^{2+}$ by light irradiation.

Technical Solution

CRY2 variants according to embodiments are CRY2 variants in which at least one of E279 and E281 having a negative charge among a $N_{277}SEGE_{281}$ sequence of SEQ ID NO: 1 is substituted with any one selected from the neutral amino acid group of alanine (A), isoleucine (I), leucine (L), valine (V), phenylalanine (F), methionine (M), and tryptophan (W), or S278 or G280 in the $N_{277}SEGE_{281}$ sequence of SEQ ID NO: 1 is substituted with any one selected from a bulky amino acid group of tryptophan (W) and phenylalanine (F).

The $Ca^{2+}$ modulator according to embodiments includes a CRY2 variant and a STIM1 protein bound to the N-terminus or C-terminus of the CRY2 variant.

Other embodiments of the present invention are included in the following detailed description.

Advantageous Effects

The CRY2 variant according to embodiments may be dimerized even under low light illumination. Therefore, it may be used as a modulator that effectively regulates the transmission of fine cellular signals in living cells.

DESCRIPTION OF THE DRAWINGS

FIG. 1 shows a polypeptide (SEQ ID NO: 1) of wild-type *Arabidopsis thaliana* cryptochrome 2 (CRY2).

FIG. 2 is a model structure showing two adjacent protruding loops of *Arabidopsis* CRY2 predicted by SWISS-MODEL.

FIG. 9 is a graph showing the average maximum R-GECO1 fluorescence level at various light densities.

MODE FOR INVENTION

Figure 3:
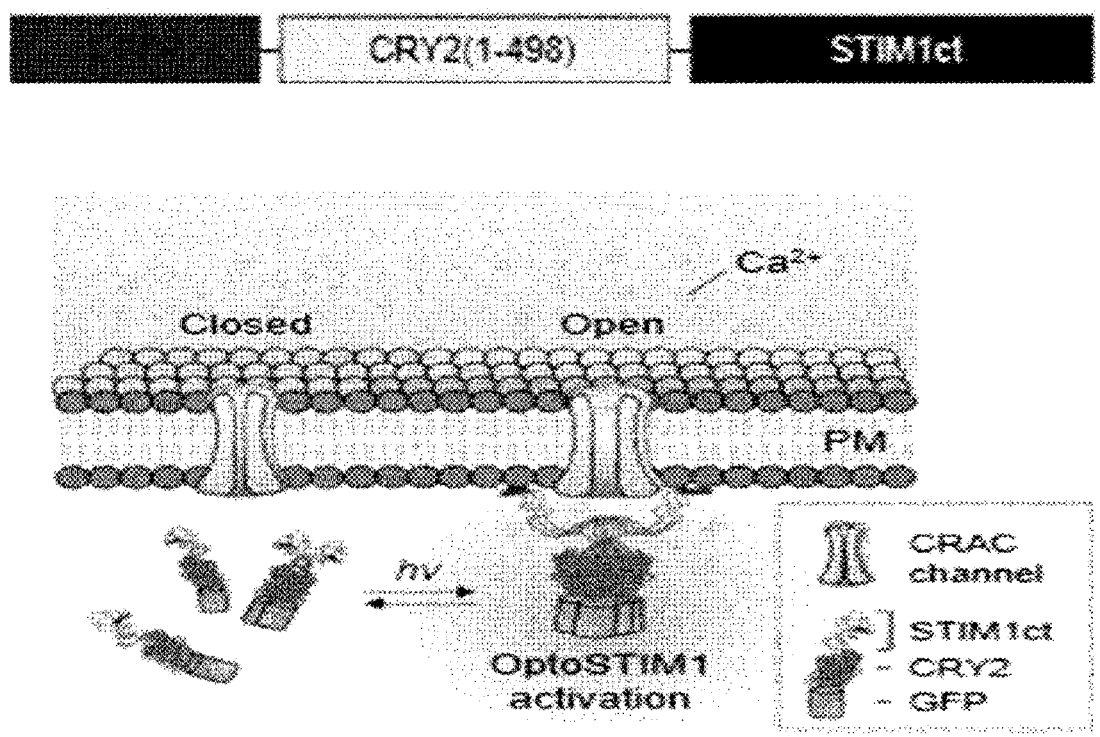
FIG. 3 is a schematic view of a $Ca^{2+}$ modulator (CRY2 variant-STIM1) and a schematic view showing an on/off mechanism of a CRAC ($Ca^{2+}$ Release Activated $Ca^{2+}$) channel by light.

Hereinafter, the embodiments will be described in detail so that those skilled in the art can easily perform the embodiments. The embodiments may be implemented in various different forms, and the present disclosure is not limited only to the specific embodiments described herein.

Unless the definition of some terms used in the present disclosure is defined otherwise below, all technical and scientific terms used herein have the same meaning as commonly understood by one of ordinary skill in the art to which the present invention belongs.

The techniques and processes described in this disclosure are generally performed according to conventional methods, which are presented throughout this application. In general, nomenclatures and experimental procedures in molecular biology, biochemistry, analytical chemistry, and cell culture used in this disclosure are well known in the art and are the same as those commonly used.

Variant

The present disclosure provides a CRY2 polypeptide that is thermally stabilized by site-specific mutagenesis. In the present disclosure, a mutation is produced by site-specific mutagenesis after rationally predicting the most optimal amino acid at a new position that is not known previously through a bioinformation analysis and protein design using a computer.

FIG. 1 shows a polypeptide (SEQ ID NO: 1) of wild-type *Arabidopsis thaliana* cryptochrome 2 (CRY2).

In the present disclosure, the term "wild-type" refers to native CRY2 having the most common amino acid sequence among members of the species. In the present disclosure, wild-type CRY2 is a polypeptide having a length of 498 amino acids (SEQ ID NO: 1, FIG. 1).

In the present disclosure, "fragment" refers to a functional fragment of a CRY2 polypeptide having CRY2 activity. In addition, it refers to a functional fragment of a CRY2 polypeptide having 85% or more sequence identity with the sequence of SEQ ID NO: 1. The fragment of the CRY2 polypeptide may also have at least one or more substitutions according to the invention. Sequence identity of at least 96%, 97%, 98%, 99%, or 100% is preferred. The fragment is intended as a polypeptide consisting only of a part of the intact polypeptide sequence and structure, and may include C-terminal or N-terminal deletion of the variant. The functional fragment may have a cell binding region and a heparin binding segment of the CRY2 protein of interest according to the present invention.

In the present disclosure, "sequence identity" means that the same amino acid residues are found in the CRY2 polypeptide according to the present invention as described above. When the specified contiguous segments of the amino acid sequence of the CRY2 polypeptide are aligned and compared with the specific amino acid sequence corresponding to the reference molecule, the wild-type *Arabidopsis thaliana* CRY2 polypeptide is used as a reference. The percentage (%) of sequence identity is calculated by measuring the number of positions in which the same amino acid residue exists in both sequences, dividing this by the total number of positions in the segment compared with the reference molecule, and multiplying this by 100 to calculate the percentage (%) of sequence identity. Sequence alignment methods are well known in the art. The reference sequence as used herein refers to the specifically corresponding wild-type *Arabidopsis* CRY2 protein according to the invention. It is desirable that the sequence identity is at least 96%, 97%, 98%, or 99% or more, or 100%. A person of an ordinary skill in the art may appreciate that the remaining 15% or less of the amino acids in the full length of the CRY2 protein according to the present invention may be variable, for example, using other sources of CRY2 species or due to suitable non-CRY2 peptide sequences generally known in the art or an addition of a tag.

The present inventors have confirmed that the protruding loop that contributes to the dimer interface of CRY2 in the wild-type *Arabidopsis thaliana* is closely related to the photosensitivity of CRY2. In particular, it has been confirmed that the $N_{277}SEGE_{281}$ sequence consisting of five amino acids in close contact between two dimerized overhanging loops plays an important role. In particular, it has been confirmed that reducing the interaction of these five amino acids may reduce the photodependence of dimerization (or homo-association).

In particular, it has been confirmed that in order to reduce potential electrostatic interactions in these sequences, photosensitivity may be increased by substituting glutamic acid (E279 or E281) having a negative charge with any one selected from the neutral (or hydrophobic) amino acid group of alanine (A), isoleucine (I), leucine (L), valine (V), phenylalanine (F), methionine (M), and tryptophan (W).

In addition, it has been confirmed that the photosensitivity may be increased by substituting S278 or G280 in $N_{277}SEGE_{281}$ with any one selected from the bulky amino acid group of tryptophan (W) and phenylalanine (F).

Accordingly, a possible variant in the present disclosure may be any one of various variants disclosed in Table 1.

TABLE 1

| Number of mutations | Type of mutation |
| --- | --- |
| 1 position mutation | E279A, E279I, E279L, E279V, E279F, E279M, E281A, E281I, E281L, E281V, E281F, E281M, S278W, S278F, G280W, G280F |
| 2 position mutations | (E279A, E281A) (E279A, E281I) (E279A, E281L) (E279A, E281V) (E279A, E281F) (E279A, E281M) (E279A, S278W) (E279A, S278F) (E279A, G280W) (E279A, G280F) (E279I, E281A) (E279I, E281I) (E279I, E281L) (E279I, E281V) (E279I, E281F) (E279I, E281M) (E279I, S278W) (E279I, S278F) (E279I, G280W) (E279I, G280F) (E279L, E281A) (E279L, E281I) (E279L, E281L) (E279L, E281V) (E279L, E281F) (E279L, E281M) (E279L, S278W) (E279L, S278F) (E279L, G280W) (E279L, G280F) (E279V, E281A) (E279V, E281I) (E279V, E281L) (E279V, E281V) (E279V, E281F) (E279V, E281M) (E279V, S278W) (E279V, S278F) (E279V, G280W) (E279V, G280F) (E279F, E281A) (E279F, E281I) |

TABLE 1-continued

| Number of mutations | Type of mutation |
|---|---|
|  | (E279F, E281L) (E279F, E281V) (E279F, E281F) (E279F, E281M) (E279F, S278W) (E279F, S278F) (E279F, G280W) (E279F, G280F) (E279M, E281A) (E279M, E281I) (E279M, E281L) (E279M, E281V) (E279M, E281F) (E279M, E281M) (E279M, S278W) (E279M, S278F) (E279M, G280W) (E279M, G280F) (E281A, S278W) (E281A, S278F) (E281A, G280W) (E281A, G280F) (E281I, S278W) (E281I, S278F) (E281I, G280W) (E281I, G280F) (E281L, S278W) (E281L, S278F) (E281L, G280W) (E281L, G280F) (E281V, S278W) (E281V, S278F) (E281V, G280W) (E281V, G280F) (E281F, S278W) (E281F, S278F) (E281F, G280W) (E281F, G280F) (E281M, S278W) (E281M, S278F) (E281M, G280W) (E281M, G280F) (278W, 280W) (278W, 280F) (278F, 280W) (278F, 280F) |
| 3 position mutations | (E279A, E281A, 278W) (E279A, E281A, 278F)(E279A, E281A, 280W) (E279A, E281A, 280F) (E279A, E281I, 278W) (E279A, E281I, 278F)(E279A, E281I, 280W) (E279A, E281I, 280F) (E279A, E281L, 278W) (E279A, E281L, 278F)(E279A, E281L, 280W) (E279A, E281L, 280F) (E279A, E281V, 278W) (E279A, E281V, 278F)(E279A, E281V, 280W) (E279A, E281V, 280F) (E279A, E281F, 278W) (E279A, E281F, 278F)(E279A, E281F, 280W) (E279A, E281F, 280F), (E279A, E281M, 278W) (E279A, E281M, 278F)(E279A, E281M, 280W) (E279A, E281M, 280F) (E279I, E281A, 278W) (E279I, E281A, 278F)(E279I, E281A, 280W) (E279I, E281A, 280F) (E279I, E281I, 278W) (E279I, E281I, 278F)(E279I, E281I, 280W) (E279I, E281I, 280F) (E279I, E281L, 278W) (E279I, E281L, 278F)(E279I, E281L, 280W) (E279I, E281L, 280F) (E279I, E281V, 278W) (E279I, E281V, 278F)(E279I, E281V, 280W) (E279I, E281V, 280F) (E279I, E281F, 278W) (E279I, E281F, 278F)(E279I, E281F, 280W) (E279I, E281F, 280F), (E279I, E281M, 278W) (E279I, E281M, 278F)(E279I, E281M, 280W) (E279I, E281M, 280F) (E279L, E281A, 278W) (E279L, E281A, 278F)(E279L, E281A, 280W) (E279L, E281A, 280F) (E279L, E281I, 278W) (E279L, E281I, 278F)(E279L, E281I, 280W) (E279L, E281I, 280F) (E279L, E281L, 278W) (E279L, E281L, 278F)(E279L, E281L, 280W) (E279L, E281L, 280F) (E279L, E281V, 278W) (E279L, E281V, 278F)(E279L, E281V, 280W) (E279L, E281V, 280F) (E279L, E281F, 278W) (E279L, E281F, 278F)(E279L, E281F, 280W) (E279L, E281F, 280F), (E279L, E281M, 278W) (E279L, E281M, 278F)(E279L, E281M, 280W) (E279L, E281M, 280F) (E279L, E281A, 278W) (E279L, E281A, 278F)(E279L, E281A, 280W) (E279V, E281A, 280F) (E279V, E281I, 278W) (E279V, E281I, 278F)(E279V, E281I, 280W) (E279V, E281I, 280F) (E279V, E281L, 278W) (E279V, E281L, 278F)(E279V, E281L, 280W) (E279V, E281L, 280F) (E279V, E281V, 278W) (E279V, E281V, 278F)(E279V, E281V, 280W) (E279V, E281V, 280F) (E279V, E281F, 278W) (E279V, E281F, 278F)(E279V, E281F, 280W) (E279V, E281F, 280F), (E279V, E281M, 278W) (E279V, E281M, 278F) (E279V, E281M, 280W) (E279V, E281M, 280F) (E279F, E281A, 280F) (E279F, E281I, 278W) (E279F, E281I, 278F)(E279F, E281I, 280W) (E279F, E281I, 280F) (E279F, E281L, 278W) (E279F, E281L, 278F)(E279F, E281L, 280W) (E279F, E281L, 280F) (E279F, E281V, 278W) (E279F, E281V, 278F)(E279F, E281V, 280W) (E279F, E281V, 280F) (E279F, E281F, 278W) (E279F, E281F, 278F)(E279F, E281F, 280W) (E279F, E281F, 280F), (E279F, E281M, 278W) (E279F, E281M, 278F) (E279F, E281M, 280W) (E279F, E281M, 280F) (E279M, E281A, 280F) (E279M, E281I, 278W) (E279M, E281I, 278F)(E279M, E281I, 280W) (E279M, E281I, 280F) (E279M, E281L, 278W) (E27M, E281L, 278F)(E279M, E281L, 280W) (E279M, E281L, 280F) (E279M, E281V, 278W) (E279M, E281V, 278F)(E279M, E281V, 280W) (E279M, E281V, 280F) (E279M, E281F, 278W) (E279M, E281F, 278F)(E279M, E281F, 280W) (E279M, E281F, 280F), (E279M, E281M, 278W) (E279M, E281M, 278F) (E279M, E281M, 280W) (E279M, E281M, 280F)(E279A, S278W, G280W) (E279A, S278W, G280W) (E279A, S278W, G280F) (E279A, S278F, G280F) (E279I, S278W, G280W) (E279I, S278F, G280W) (E279I, S278W, G280F) (E279I, S278F, G280F) (E279L, S278W, G280W) (E279L, S278W, G280F) (E279L, S278F, G280F) (E279V, S278W, G280W) (E279V, S278F, G280W) (E279V, S278W, G280F) (E279V, S278F, G280F) (E279F, S278W, |

TABLE 1-continued

| Number of mutations | Type of mutation |
|---|---|
| | G280W) (E279F, S278F, G280W) (E279F, S278W, G280F) (E279F, S278F, G280F) (E279M, S278W, G280W) (E279M, S278F, G280W) (E279M, S278W, G280F) (E279M, S278F, G280F) (E281A, S278W, G280W) (E281A, S278F, G280W) (E281A, S278W, G280F) (E281A, S278F, G280F) (E281I, S278W, G280W) (E281I, S278F, G280W) (E281I, S278W, G280F) (E281I, S278F, G280F) (E281L, S278W, G280W) (E281L, S278F, G280W) (E281L, S278W, G280F) (E281L, S278F, G280F) (E281V, S278W, G280W) (E281V, S278F, G280W) (E281V, S278W, G280F) (E281V, S278F, G280F) (E281F, S278W, G280W) (E281F, S278F, G280W) (E281F, S278W, G280F) (E281F, S278F, G280F) (E281M, S278W, G280W) (E281M, S278F, G280W) (E281M, S278W, G280F) (E281M, S278F, G280F) |
| 4 position mutations | (E279A, E281A, S278W, G280W) (E279A, E281I, S278W, G280W) (E279A, E281L, S278W, G280W) (E279A, E281V, S278W, G280W) (E279A, E281F, S278W, G280W) (E279A, E281M, S278W, G280W) (E279I, E281A, S278W, G280W) (E279I, E281I, S278W, G280W) (E279I, E281L, S278W, G280W) (E279I, E281V, S278W, G280W) (E279I, E281F, S278W, G280W) (E279I, E281M, S278W, G280W) (E279L, E281A, S278W, G280W) (E279L, E281I, S278W, G280W) (E279L, E281L, S278W, G280W) (E279L, E281V, S278W, G280W) (E279L, E281F, S278W, G280W) (E279L, E281M, S278W, G280W) (E279V, E281A, S278W, G280W) (E279V, E281I, S278W, G280W) (E279V, E281L, S278W, G280W) (E279V, E281V, S278W, G280W) (E279V, E281F, S278W, G280W) (E279V, E281M, S278W, G280W) (E279F, E281A, S278W, G280W) (E279F, E281I, S278W, G280W) (E279F, E281L, S278W, G280W) (E279F, E281V, S278W, G280W) (E279F, E281F, S278W, G280W) (E279F, E281M, S278W, G280W) (E279M, E281A, S278W, G280W) (E279M, E281I, S278W, G280W) (E279M, E281L, S278W, G280W) (E279M, E281V, S278W, G280W) (E279M, E281F, S278W, G280W) (E279M, E281M, S278W, G280W) |

Among the various mutations mentioned in Table 1, the mutation in which E281 is substituted with any one selected from a neutral (or hydrophobic) amino acid group of alanine (A), isoleucine (I), leucine (L), valine (V), phenylalanine (F), methionine (M), and tryptophan (W) is most effective in enhancing the photosensitivity, which is proven by the fact that E281 is structurally and most closely positioned in the two adjacent protruding loop structures (structure predicted by SWISS-MODEL) of *Arabidopsis* CRY2 shown in FIG. 2.

Meanwhile, when an insertion sequence consisting of at least 7 to 9 amino acids (CRY2clust) selected from the group of arginine (R), aspartic acid (D), proline (P), asparagine (N), alanine (A), and leucine (L) at the carboxy terminal of SEQ ID NO: 1 illustrated in FIG. 1 is additionally inserted, the photosensitivity may be increased more synergistically.

The specific insertion sequence (CRY2clust) may be SEQ ID NOs: 2 to 16 in Table 2.

The effects of these insertion sequences (CRY2clust) are disclosed in KR2019-0000080 which is the prior application of the present inventor, and the contents are incorporated herein.

TABLE 2

| | SEQ ID NO: | Sequence |
|---|---|---|
| 9 amino acid insertion (A9) | 2 | ARDPPDLDN |
| | 3 | ARDPPDIDN |
| | 4 | ARDPPDADN |
| | 5 | ARDPPDKDN |
| | 6 | ARDPPDDDN |

TABLE 2-continued

| | SEQ ID NO: | Sequence |
|---|---|---|
| 8 amino acid insertion (A8) | 7 | ARDPDLDN |
| | 8 | ARDPDIDN |
| | 9 | ARDPDADN |
| | 10 | ARDPDKDN |
| | 11 | ARDPDDDN |
| 7 amino acid insertion (A7) | 12 | ARDPPDL |
| | 13 | ARDPPDI |
| | 14 | ARDPPDA |
| | 15 | ARDPPDK |
| | 16 | ARDPPDD |

$Ca^{2+}$ Modulator

FIG. 3 is a schematic view of the $Ca^{2+}$ modulator and the on/off mechanism of the CRAC (Ca2 Release Activated $Ca^{2+}$) channel by light.

A $Ca^{2+}$ modulator (hereinafter, OptoSTIM1) may be constructed by fusing a protein of a STIM1 (Stromal Interaction Molecule 1) protein that may control the on/off of a CRAC ($Ca^{2+}$ Release Activated $Ca^{2+}$) channel and a CRY2 variant according to the embodiment. EGFP is a protein fused to fluorescently confirm the operation of the Ca2 modulator.

When CRY2 is dimerized by light (hv), STIM1 is also homo-associated, and the homo-associated STIM1 turns on the CRAC channel and causes a flux of $Ca^{2+}$ ions into the cell.

The reaction by light is reversible, and when the light is removed, CRY2 is separated into monomers, and finally STIM1 is also separated into monomers, and CRAC is closed.

Since the CRY2 variant according to the embodiments constituting the $Ca^{2+}$ modulator according to the embodiments may dimerize only with low light irradiation, it is possible to operate even when light is irradiated to cells in a non-invasive manner. In particular, the $Ca^{2+}$ modulator including the $CRY2^{E281A}$-A9 variant with the best photosensitivity is called monSTIM1.

The specific mechanism and sequence of STIM1 are described in papers (Soboloff, J. et al. Nat Rev Mol Cell Biol 13, 549-565 (2012).

Hereinafter, preferred experimental examples are presented to aid the understanding of the present invention, but the following experimental examples are only illustrative of the present invention, and the scope of the present invention is not limited to the following examples.

Experiment Method

Plasmid Construction

In these experimental examples, OptoSTIM1 encompasses the photolyase homology region (PHR) and STIM1 (amino acids 238-668) at the C-terminus of CRY2 (amino acids 1-498), and mutagenesis was induced through PCR (Polymerase Chain Reaction) using mutagenesis oligonucleotides in forward and reverse directions corresponding to each and two flanking primers. It was mutated through the polymerase chain reaction of CRY2 ( )-driven overlap extension. The flanking primers and mutagenesis oligonucleotides used for mutagenesis of CRY2 are as follows:

flanking primer, 5'-GTA ACC GGT CAT GAA GAT GGA CAA AAA GAC CAT CGT CTG-3 '(forward direction) (SEQ ID NO: 17) and 5'-CTC CGC CTC CCC CAC TGA ATT CGG CAG CAC CGA TCA TAA TC-3 '(reverse direction) (SEQ ID NO: 18)

E279A, 5'-AAC AGC GCC GGC GAA GAA AGC GCC GAT CTG TTC CTG-3 '(forward direction) (SEQ ID NO: 19) and 5'GCT TTC TTC GCC GGC GCT GTT TTT ATC GCG AGC CCA-3'(reverse direction) (SEQ ID NO: 20)

G280W, 5'AAC AGC GAA TGG GAA GAA AGC GCC GAT CTG TTC C-3 '(forward direction) (SEQ ID NO: 21) and 5'-GCT TTC TTC CCA TTC GCT GTT TTT ATC GCG AGC CCA-3'(reverse direction) (SEQ ID NO: 22)

E281A, 5'-GAA GGC GCC GAA AGC GCC GAT CTG TTC CTG-3 '(forward direction SE ID NO: 23 and 5'-GCT TTC GGC GCC TTC GCT GTT TTT ATC GCG AG-3' (reverse direction) (SEQ ID NO: 24)

flanking primer,
(forward direction)
(SEQ ID NO: 17)
5'-GTA ACC GGT CAT GAA GAT GGA CAA AAA GAC CAT CGT CTG-3'
and (reverse direction)
(SEQ ID NO: 18)
5'-CTC CGC CTC CCC CAC TGA ATT CGG CAG CAC CGA TCA TAA TC-3'

E279A,
(forward direction)
(SEQ ID NO: 19)
5'-AAC AGC GCC GGC GAA GAA AGC GCC GAT CTG TTC CTG-3' and (reverse direction)
(SEQ ID NO: 20)
5'GCT TTC TTC GCC GGC GCT GTT TTT ATC GCG AGC CCA-3'

G280W,
(forward direction)
(SEQ ID NO: 21)
5'AAC AGC GAA TGG GAA GAA AGC GCC GAT CTG TTC C-3'
and (reverse direction)
(SEQ ID NO: 22)
5'-GCT TTC TTC CCA TTC GCT GTT TTT ATC GCG AGC CCA-3'

E281A,
(forward direction)
(SEQ ID NO: 23)
5'-GAA GGC GCC GAA AGC GCC GAT CTG TTC CTG-3'
and (reverse direction)
(SEQ ID NO: 24)
5'-GCT TTC GGC GCC TTC GCT GTT TTT ATC GCG AG-3'

The PCR-amplified sequence encoding the CRY2 variant was cloned into the OptoSTIM1 (CRY2) vector at AgeI and EcoRI sites or BspEI and BamHI sites. OptoSTIM1 including oligomer variants CRY2olig (E490G) and CRY2clust (A9) was also constructed in the same way. For construction of OptoSTIM1 having both CRY2 E281A and oligomer variants (E490G or A9), the sequence encoding the CRY2 (E281A) variant was inserted into OptoSTIM1 (CRY2-A9) or OptoSTIM1 (CRY2 E490G) at the AgeI and SacI sites.

Cell Culture and Transfection

HeLa cells and HEK293T (ATCC) were maintained in DEME (Dulbecco's Modified Eagle's Medium, PAA Laboratories GmbH) medium supplemented with 10% fetal bovine serum (FBS; Invitrogen) at 37° C. in a humidified 10% $CO_2$ atmosphere. Cells were transfected using a microporator (Neon Transfection System; Invitrogen) or Lipofectamine LTX (Invitrogen) according to the manufacturer's instructions.

Live-Cell Imaging

The prepared cells were plated on a 96-well polymer cover slip bottom plate (μ-plate 96 well ibiTreat; ibidi). R-GECO1 fluorescence imaging using blue light illumination for OptoSTIM1 activation is performed using a Nikon A1R confocal microscope (Nikon Instruments) which is mounted on an inverted Eclipse Ti body (Nikon) and mounted with a CFI Plan Apochromat VC objective (60×/1.4 numerical aperture (NA)) and digital zoom Nikon imaging software (NIS Element AR 64-bit version 3.21; laboratory imaging). During image processing, cells were maintained at 10% $CO_2$ and 37° C. by culturing in a Chamlide TC system (Live Cell Instruments, Inc., Korea). Immediately before imaging, the medium was replaced with OPTIMEM (Invitrogen). For blue light photo excitation (power density, 500 μW $mm^{-2}$), a 488 nm laser was delivered at intervals of 5 seconds for 1 minute.

Fura-2 Imaging and Calibration

HeLa cells were incubated with Fura-2 AM (Invitrogen) for 30 minutes at room temperature and loaded, and then dissolved in dimethyl sulfoxide, diluted into 2 μM in DMEM, and washed three times for 5 minutes in each step. Fura-2 imaging was performed by intermittent excitation using a 340 nm and 380 nm filtered fluorescent lamp with a LAMBDA DG-4 lamp (Sutter Instrument Company) and a 40×/0.75 NA CFI Plan Fluor objective lens. Light emitted through a 510 nm emission filter was collected with a Nikon DS-Qi1 black and white digital camera. Free [$Ca^{2+}$] was calculated according to a formula $[Ca2+]_{free}=Kd_{EGTA}\times(R-R_{min})/(R_{max}-R)\times F380_{max}/F380_{min}$, where $Kd_{EGTA}$ Is a dissociation constant of Fura-2, $R_{min}$ and $R_{max}$ are ratios at zero free $Ca^{2+}$ and saturated $Ca^{2+}$, and $F380_{max}$ and $F380_{min}$ are respectively fluorescence intensity for zero free $Ca^{2+}$ and saturated free $Ca^{2+}$ at a wavelength of 380 nm. $Kd_{EGTA}$ was determined using a Fura-2 $Ca^{2+}$ imaging calibration kit (Invitrogen) according to the manufacturer's instructions.

Animal Experiment

Mice were treated and managed according to guidelines of the KAIST Animal Care and Use Committee (Daejeon). In-vivo mouse experiments were performed in 8 to 13 week-old male C56BL/6J mice purchased from Jackson Laboratory. The mice were housed in a cage with free access to food pellets and water and maintained in a 12-hour light/dark cycle (8 am to 8 pm) at 22° C. and 40% humidity. All behavioral experiments were performed at the same time of day during the light phase of the light/dark cycle.

Preparation of Lentivirus

Plasmids for lentiviral vectors including the CaMKIIβ promoter were prepared as described in the plasmid construct description. AgeI and EcoRI sites were used to prepare plasmids for other variants by cloning exchange PCR-amplified CRY2 variants ($CRY2^{E281A}$-A9, $CRY2^{D387A}$) into pLenti-CaMKIIα-EGFP-CRY2-STIM1. PacI and BamHI sites were used to prepare plasmids including a GfABC1 D promoter by cloning and exchanging a PCR-amplified GfABC1 D promoter in pLenti-CaMKIIβ-EGFP-CRY2-STIM1. The lentiviral vectors with VSV-G and Δ8.9 required for lentiviral production were co-transfected into the HEK293T cell line by using a PEI transfection reagent. After 72 hours' transfection, a supernatant was collected therefrom, centrifuged at 2000 rpm for 5 minutes, and then filtered through a 0.45 μM filter unit (millipore). For purification of lentivirus, ultracentrifugation (25,000 rpm) was performed at 4° C. for 2 hours. After the ultracentrifugation, the supernatant was removed, and pellets were resuspended in phosphate buffered saline (PBS), aliquoted, and stored at −80° C. The lentivirus was titrated by using a Lenti-X™ qRT-PCR titration kit (Takara Bio Inc.) according to the manufacturer's instructions. Virus titers were respectively $7.88\times10^{11}$ and $2.23\times10^{12}$ genome copies $ml^{-1}$ for CaMKIIα promoter-containing OptoSTIM1 and monSTIM1 viruses and $6.81\times10^{11}$ and $8.42\times10^{11}$ genome copies $ml^{-1}$ for GfABC1 D promoter-containing monSTIM1 and OptoSTIM1 ($CRY2^{D387A}$).

Stereotactic Injection and in vivo Photomagnetic Light Stimulation Conditions 8 week-old male C57BL/6J mice were used for stereotactic virus injection. A surgical procedure was performed according to the stereotactic guidelines. Before the surgery, surgical instruments were sterilized at 240° C. in a hot bead sterilizer. All mice maintained at 37° C. using a temperature controller (Live Cell Instrument) were anesthetized with 0.022 ml/g of Avertin and placed in a stereotactic apparatus (Neurostar GmbH, Germany). The following coordinates (for Bregma) were used for optical stimulation: somatosensory cortex (S1): 1.0 mm anteroposterior (AP), 2.2 mm medial (ML) and −1.2 to −0.7 mm dorsal germ (DV); ACC: 1.0 mm AP, 0.3 mm ML and −1.0 mm DV; Dorsal hippocampus (HPC): −2.0 mm AP, 1.3 mm ML and 1.8 mm DV; and Sagittal (TH): −1.0 mm AP, 1.3 mm ML and 3.4 mm DV. The lentivirus was injected at 0.075 μl/min by using a 10 μl Hamilton microsyringe (Hamilton Avertin Company, USA) and a 33-gauge injection needle (NanoFil Needle Assortment, blunt; World Precision Instruments, USA). After the injection, the needle was kept in place for 10 minutes before withdrawn stepwise (0.2 mm per step, 1 s each). Four weeks after the injection, an optogenetic stimulation experiment was performed using light of 473 nm transmitted by a solid LED excitation system (Live Cell Instrument). A duration of the light illumination for observational fear learning and immunohistochemistry experiments was 30 minutes.

Histological Treatment and Immunohistochemistry

One hour after the light illumination (except for experiments conducted under dark conditions), mice were anesthetized with 0.022 ml/g of Avertin and then perfused transcardially with phosphate buffered saline (PBS), and subsequently, 10 ml of 4% paraformaldehyde in PBS. Brains of the mice were extracted and incubated overnight at 4° C. in 4% PFA. The brains were transferred to PBS, and 60-μm coronal slices were prepared therefrom by using Vibratome (Leica Biosystems). For immunostaining, the slices were placed in PBS containing 0.2% Triton X-100 and 5% normal goat serum for 1 hour, and the solution was replaced with a primary antibody diluted in PBS containing 0.1% Triton X-100 and 2% normal goat serum. After incubation at 4° C. overnight, the slices were rinsed 5 times with PBS containing 0.2% Tween 20 (10 minutes each) and incubated with a secondary antibody for 1 hour. Subsequently, tissue sections were washed with PBS containing 0.2% Tween 20, and then mounted on a microscope slide by using a medium mounted with a Vectashield anti-fade containing DAPI (Vector Laboratories). A Nikon A1R confocal microscope (Nikon Instruments) was used to capture a fluorescence image with 10× and 60× objective lenses. All 60× images were acquired as z-stacks by binning a 3 μm depth per image plane. Antibodies used in immunohistochemistry are as follows:

A chicken anti-GFP primary antibody (1:2000, Thermo Fisher Scientific Inc.) and an Alexa 488-conjugated anti-chicken secondary body (1:2000, Thermo Fisher Scientific Inc.) variant were used to stain EGFP-CRY2 (variant)-STIM1, and a rabbit polyclonal anti-c-Fos primary antibody (1:1000; Abcam plc) and an Alexa 594-conjugated anti-rabbit secondary antibody (1:2000; Thermo Fisher Scientific Inc.) were used. In order to analyze c-Fos+ cells, the present inventors measured at least 5 coronal brain sections from each mouse sample to calculate the number of c-Fos+ cells containing DAPI+ and enclosed EGFP signals. Statistical significance thereof was evaluated by using "Sidak's Multiple Comparison Test."

Fear of Observation

An observational fear-conditioning test was performed in a chamber consisting of two identical chambers (18 cm×17.5 cm×38 cm) separated in the middle of the two chambers by a transparent Plexiglas glass dispenser. A cage was constructed to have a bottom made of 5 mm stainless steel rods with 1 cm spacing, which is similar to that of a passive feature cage (Coulbourn Instruments, LLC). A space under the rods was allowed to share sounds and smells during the experiment. Before starting the observational fear learning experiment, mice were treated for 10 minutes over 3 days. On the test day, the mice were habituated to a behavioral chamber for 1 hour right before the test. For transcranial light stimulation, observer mice were illuminated with blue light (1 mW $cm^2$) for 30 minutes, and then transferred from the chamber to another device chamber housing other mice (demonstrator mice). As the demonstrator mice, equally-stained (C57BL/6J) 10 to 12 week-old mice were used. In all experiments, the observer and demonstrator mice were not biologically related and were housed in separate cages. After acclimating the observer and demonstrator mice to a device for 5 minutes, a programmed animal shocker (Coulbourn Instruments LLC.) was used to deliver a 2 second-foot shock (1 mA) to the demonstrator mice alone at 10 second intervals for 4 minutes. On the second day (24 hours after the training), the observer mice were placed in the same chamber used for the observational fear learning to access a context memory test and then observed for 4 minutes. Fear reactions of the mice were video-recorded and quantified. The data were not blindly obtained, but reliability of the results was confirmed by two other blinded investigators. Statistical significance thereof was evaluated by using a "Tukey's test."

Open Field Test

Immediately before a test session, all mice were habituated to the laboratory for 30 minutes. The mice were illuminated with blue light (473 nm) for 1 hour at power density of 1 mW cm$^2$ to activate OptoSTIM1 transcranially, and then sequentially transferred to an open-field box during the 30 minutes' test session. A total distance traveled from the center, a speed, and a time were quantified by using an automatic infrared ray (IR) detection system (Optimousel). Statistical significance thereof was assessed by using a "Tukey's multiple comparisons test."

Quantification and Statistical Analysis

Images were captured and analyzed by using laboratory imaging software, NIS-Elements AR 64 bit version 3.21, provided by Nikon Corp. R-GECO1 intensity changes were quantified by using a time-measuring tool. Initial intensity of R-GECO1 was set to 100 and 500 (A.U.), which was previously used. Critical density of light required for activation of an OptoSTIM1 variant was determined based on at least 2 changes of fluorescence intensity of R-GECO1.

A maximum standard deviation of the R-GECO1 intensity in cells expressing the OptoSTIM1 variant within 1 minute of imaging without light stimulation was 0.187973. Accordingly, the maximum standard deviation may be less than a probability of $10^{-6}$ of a Type I error in detecting the activation, when at least 2 changes are taken as an activation limit, which corresponds to a detection limit in the previous study, and basal R-GECO1 fluorescence intensity, which is greater than 50, is also taken. Statistical significance was evaluated by a "two-tailed Student's t-test."

Experiment Results

Measurement of Ca$^{2+}$ Basal Concentration

Figure 4:
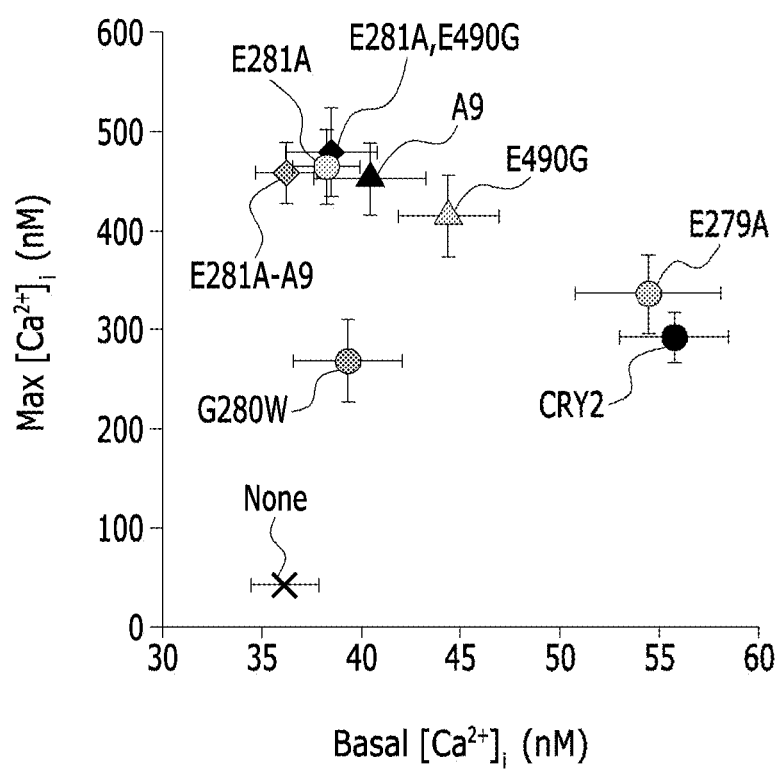
FIG. 4 is a graph showing a correlation between light stimulation $[Ca^{2+}]_i$ (x-axis, dark state) and $[Ca^{2+}]_i$ (y-axis, light stimulation) measured using Fura-2 in a $Ca^{2+}$ modulator including a CRY2 variant.

FIG. 4 is a graph showing a correlation between light stimulation [Ca$^{2+}$]$_i$ (x-axis, dark state) and [Ca$^{2+}$]$_i$ (y-axis, light stimulation) measured using Fura-2 in a Ca$^{2+}$ modulator including a CRY2 variant.

Referring to the result of FIG. 4, compared with wild-type CRY2 and E297A variant, G280W, E281A, A9 (SEQ ID NO: 2), (E281A, E490G), and (E281A-A9) exhibited a low concentration of basal [Ca$^{2+}$]$_i$ but a high concentration of maximum [Ca$^{2+}$]$_i$ due to the light stimulation, and accordingly, the activation of STIM1 by a light-based dimer turned out to work properly.

Measurement of Activation and Deactivation Rate

Figure 5:
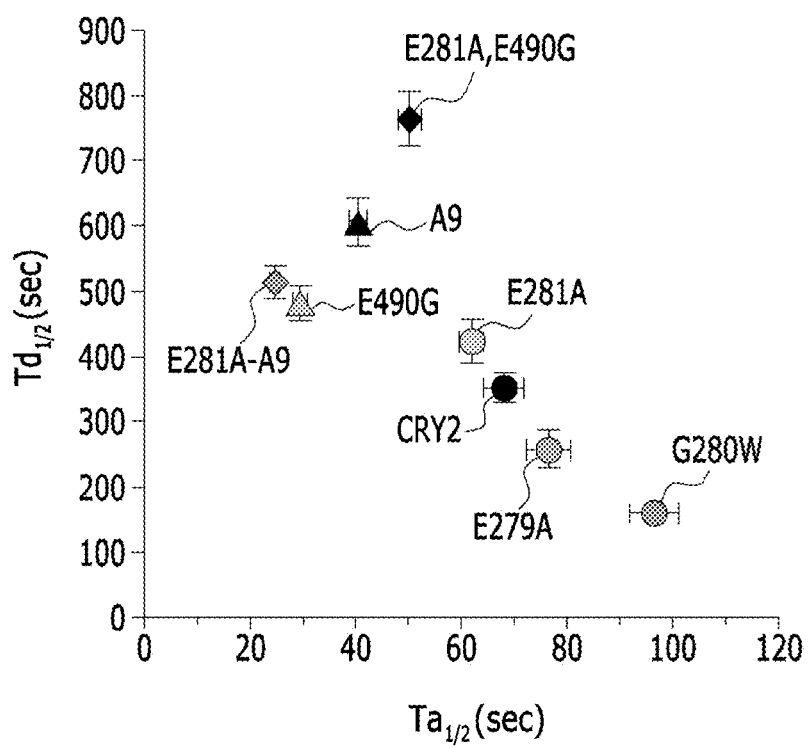
FIG. 5 is a plot showing a correlation between the half-maximal time point (x-axis) for reaching saturated R-GECO1 levels upon light stimulation and basal R-GECO1 levels in the dark (y-axis) for each indicated strain (n≥100 for each strain).

FIG. 5 is a plot showing the correlation between the half-maximal time point (x-axis) for reaching saturated R-GECO1 levels upon light stimulation and basal R-GECO1 levels in the dark (y-axis) for each indicated strain (n 100 for each strain).

Referring to FIG. 5, E281A produced higher maximum [Ca$^{2+}$]$_i$ after the stimulation, compared with other variants, but exhibited similar dynamics of activation (Tai/2=62 s) and inactivation (Td$_{1/2}$=7 min) to those of original CRY2. E281A-A9 exhibited the longest inactivation time.

Photosensitivity Measurement

FIGS. 6 to 9 are diagrams showing results of measuring photosensitivity.

Figure 6:
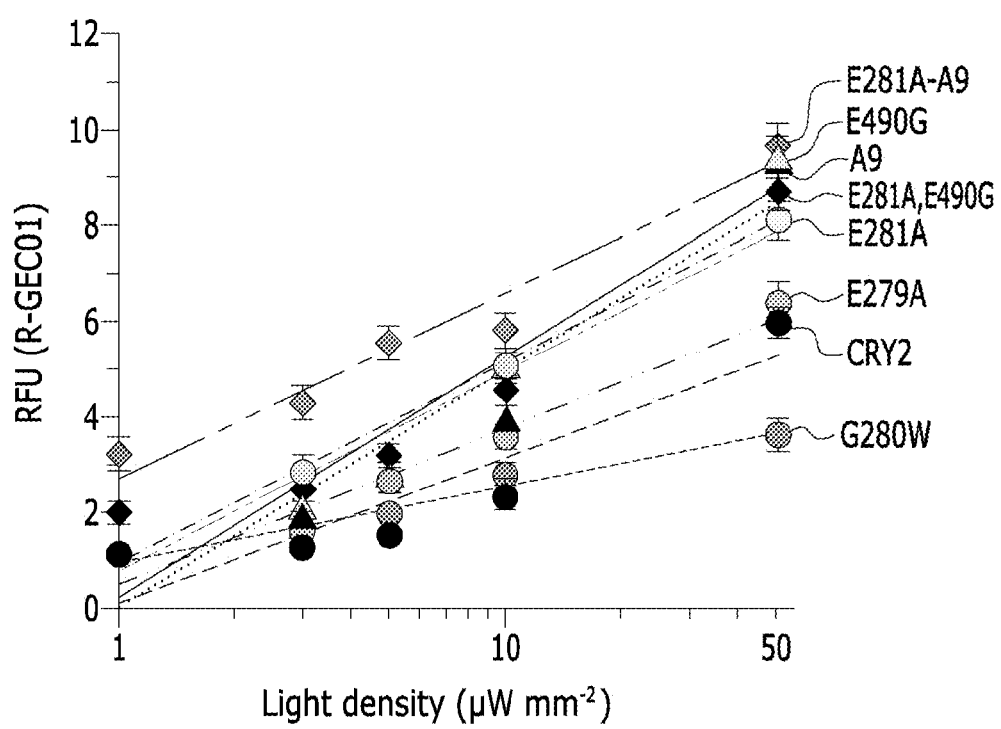
FIG. 6 is a graph showing the maximum R-GECO1 fluorescence intensity based on various light densities (1 to 50 μW mm$^{-2}$).

FIG. 6 is a graph showing the maximum R-GECO1 fluorescence intensity based on various light densities (1 to 50 μW mm$^{-2}$). In FIG. 6, blue light was delivered at 5 second intervals for one minute by using a 488 nm laser (n≥100 for each strain at each optical density) at each indicated power density.

Figure 7:
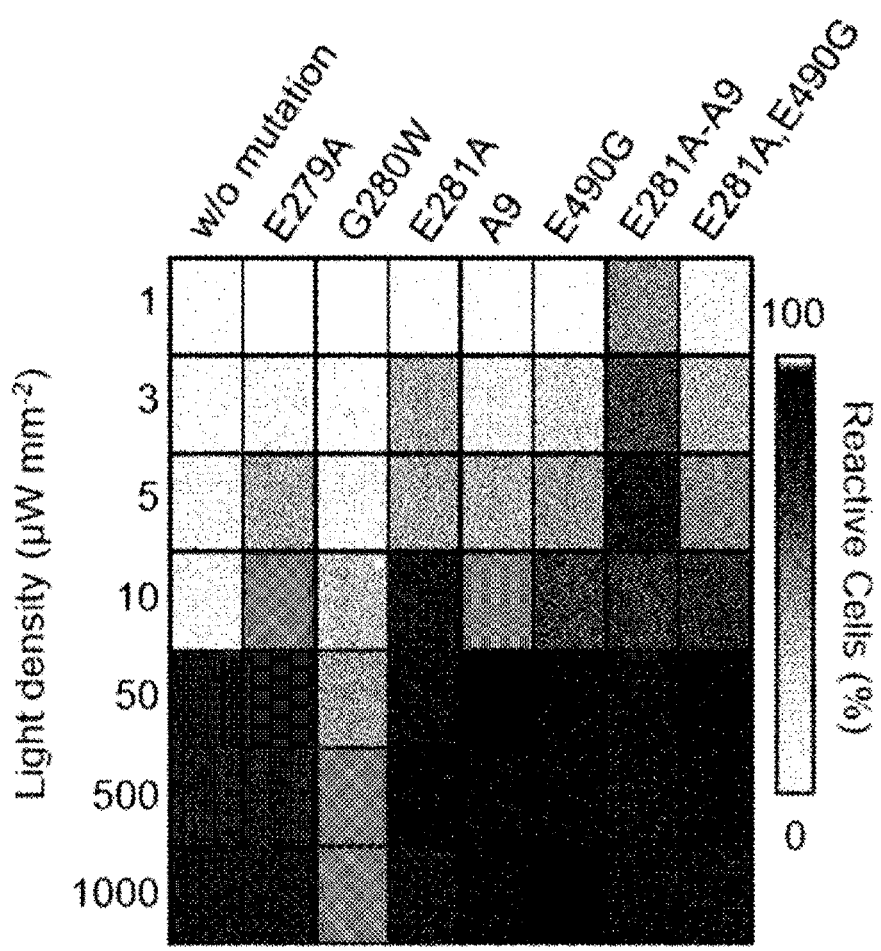
FIG. 7 is a heat plot showing the degree of responsive cell population upon light stimulation at each indicated light density.
Figure 8:
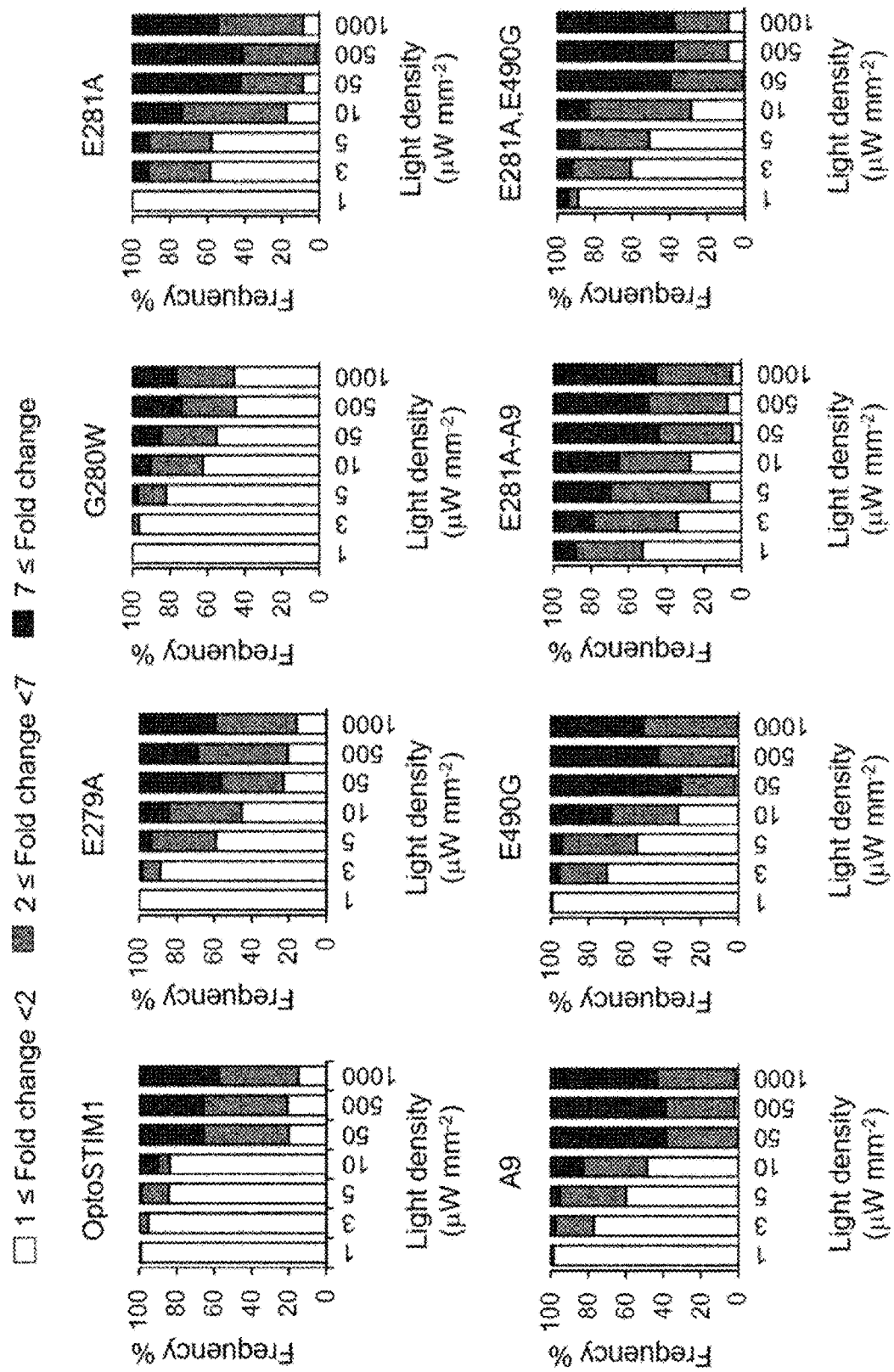
FIG. 8 is a graph showing the efficiency of $Ca^{2+}$ introduction induced upon stimulation with different light densities.

FIG. 7 is a heat plot showing the degree of responsive cell population upon light stimulation at each indicated light density. FIG. 8 is a graph showing the efficiency of Ca$^{2+}$ introduction induced upon stimulation with different light densities. FIG. 9 is a graph showing the average maximum R-GECO1 fluorescence level at various light densities.

Referring to the results of FIGS. 6 to 9, in a N$_{277}$SEGE$_{281}$ sequence, when E279 or E281 was mutated, the variant effectively reacted even to low light density and remained and thus exhibited higher photosensitivity, compared with wild CRY2. Among them, monSTIM1 (CRY2$^{E281A}$-A9) exhibited much higher sensitivity to light in that about 47% of expression cells effectively responded to light intensity of 1 μW mm$^{-2}$ and remained, which is about 55 times higher sensitivity than that of CRY2.

Non-Invasive Light Stimulation

Figure 10:
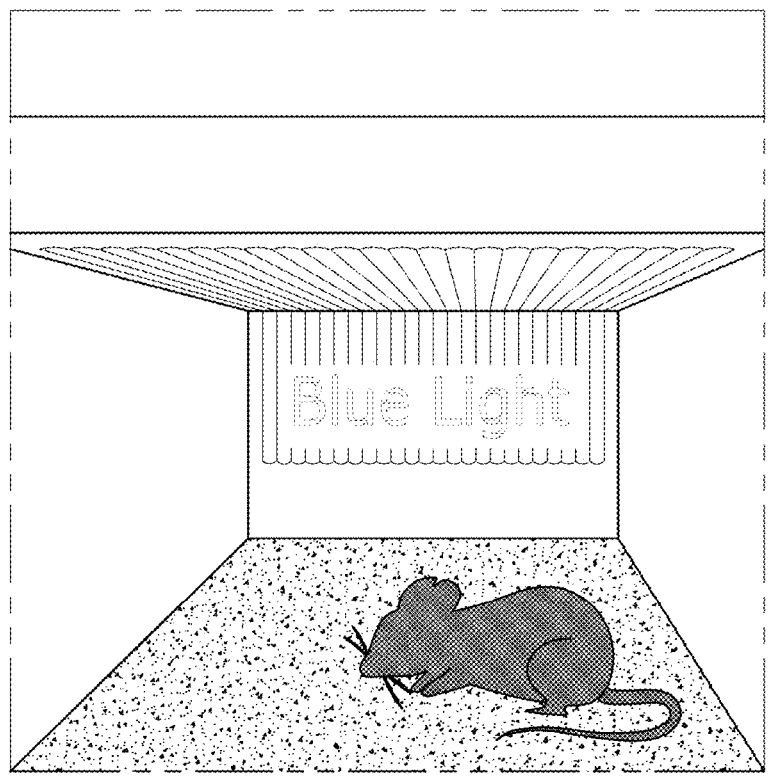
FIG. 10 shows a custom transcranial illumination system.

In order to examine whether monSTIM1 may respond to non-invasive light illumination to induce Ca$^{2+}$-dependent molecular activation in intact brain neurons, a light illumination cage was designed to have an LED solid state array attached on the cage lid capable of delivering about 1 mW cm$^{-2}$ of blue light to a mouse's head (FIG. 10). Through video reading, light itself turned out to not cause abnormal behavior or movement of mice in the cage.

Figure 11:
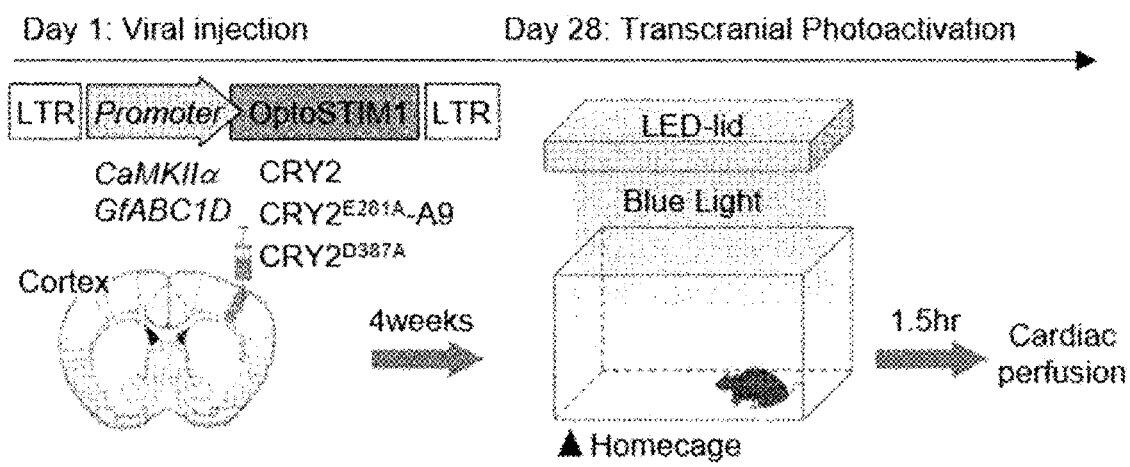
FIG. 11 is a schematic view showing the expression and activation of $Ca^{2+}$ modulators by non-invasive light stimulation.
Figure 12:
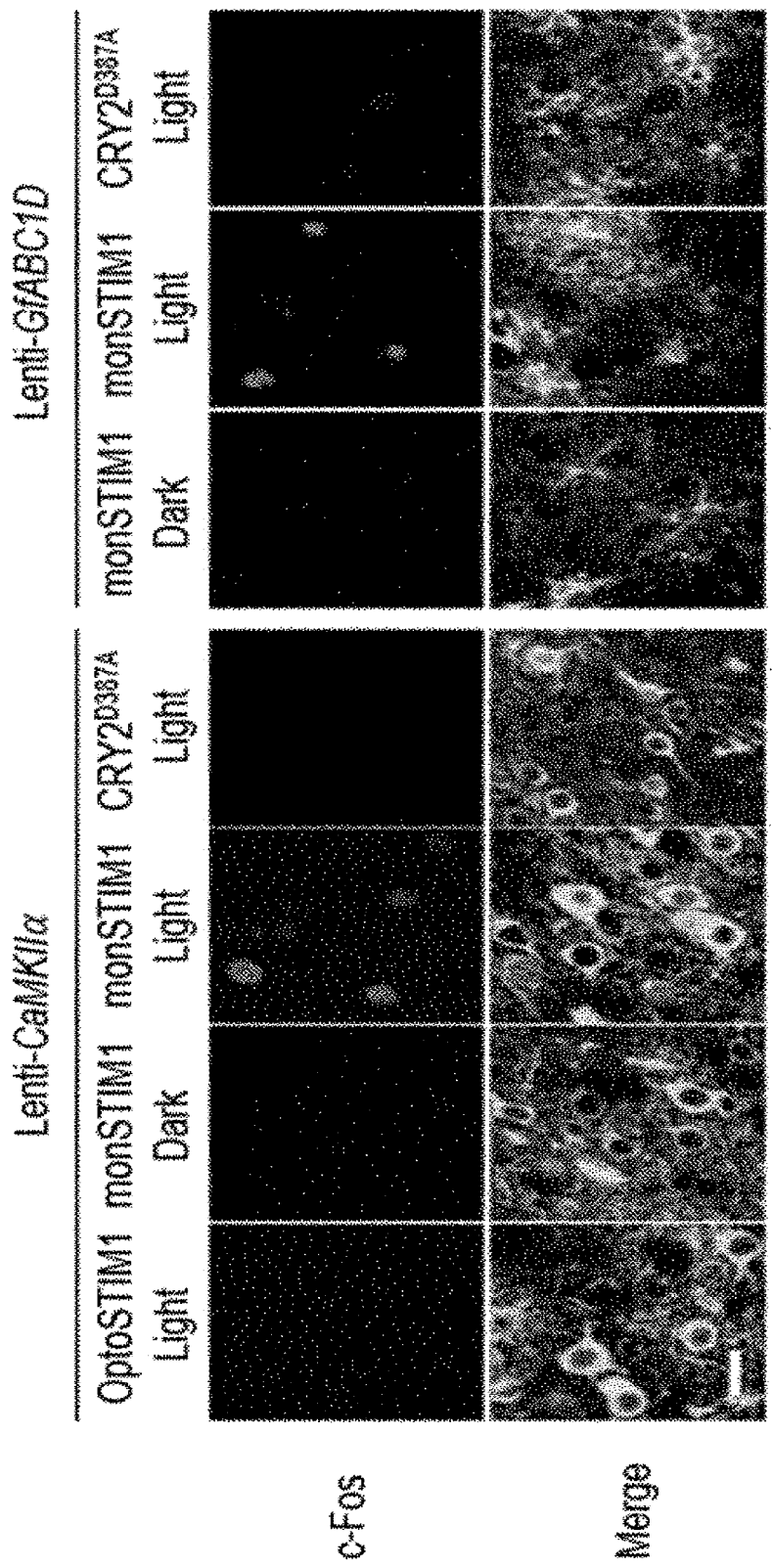
FIG. 12 is images showing c-Fos-positive cells.
Figure 13:
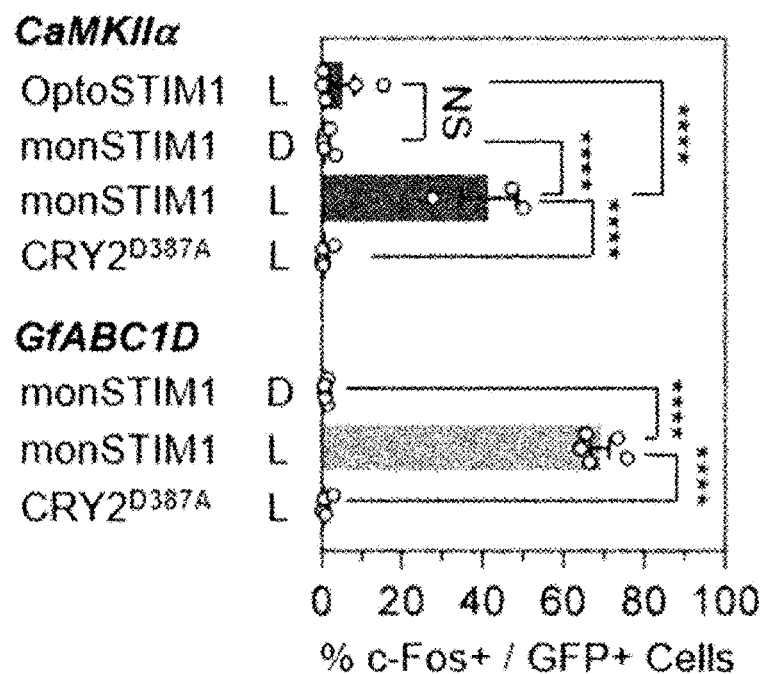
FIG. 13 is a summary chart showing a quantified population of c-Fos-positive (+) cells expressing the OptoSTIM1 variant. (P<0.0001; Sidak's tests).

Subsequently, as shown in FIG. 11, expression and activation of Ca$^{2+}$ modulators were performed by the non-invasive light stimulation. Four weeks after injecting lentivirus packaged with different OptoSTIM1 variants expressed under the control of a CaMKIIα promoter (exciting neurons) or a GfABC1 D promoter (astrosites) targeting an S1 cortical region, the mice were illuminated with LED light in a home cage and then sacrificed. Subsequently, the exciting neurons in the somatosensory cortex (S1) were transduced into lentiviral constructs of OptoSTIM1 (CRY2), monSTIM1 (CRY2$^{E281A}$-A9), or OptoSTIM1 (CRY2$^{D387A}$), which are insensitive to light. After 4 weeks, the mice were exposed to blue light for 30 minutes without removing or shaving the skin, and one hour later they were sacrificed, and then evaluated with respect to an expression level of c-Fos, a Ca$^{2+}$-dependent immediate initial gene, and the results are shown in FIGS. 12 and 13. Referring to FIGS. 12 and 13, mice expressing monSTIM1 exhibited significant induction of c-Fos expression, compared with the control group, and c-Fos signals were predominantly localized in cells expressing monSTIM1. Subsequently, functionality of monSTIM1 in astrocytes, another major cell type of a brain, was verified. Activation of monSTIM1 expressed under a control of the GfABC1 D promoter efficiently induced expression of c-Fos. Specifically, c-Fos was detected in 74% of the astrocyte population expressing monSTIM1, but in the control group, c-Fos was not noticeably induced.

Figure 14:
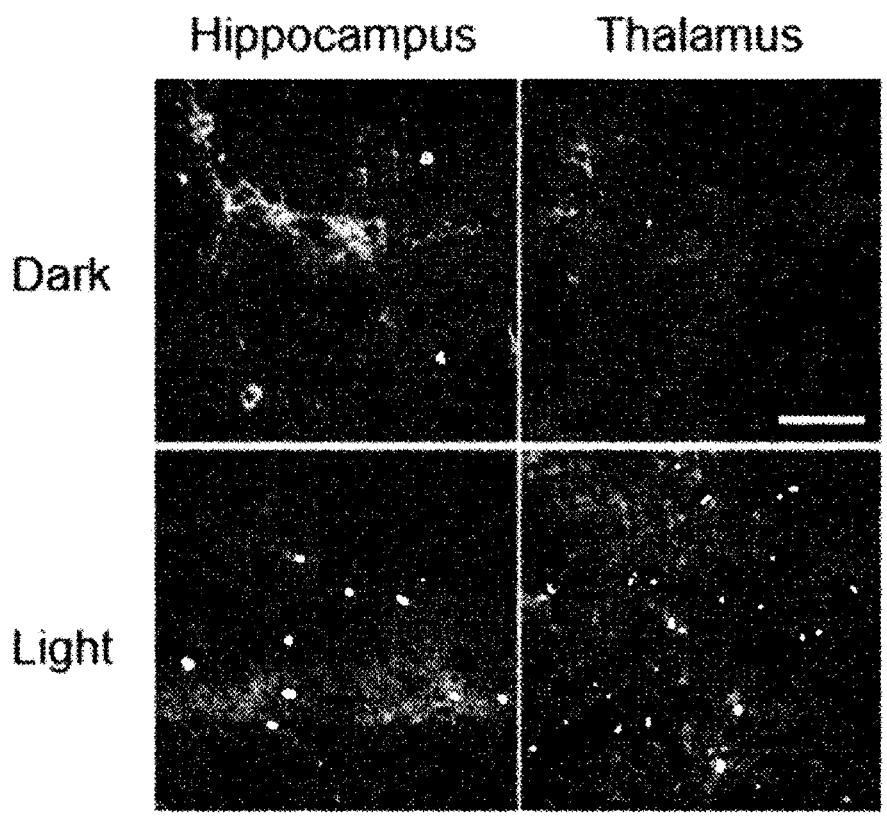
FIG. 14 shows images of c-Fos stained cells with or without monSTIM1 activation in two different brain regions.
Figure 15:
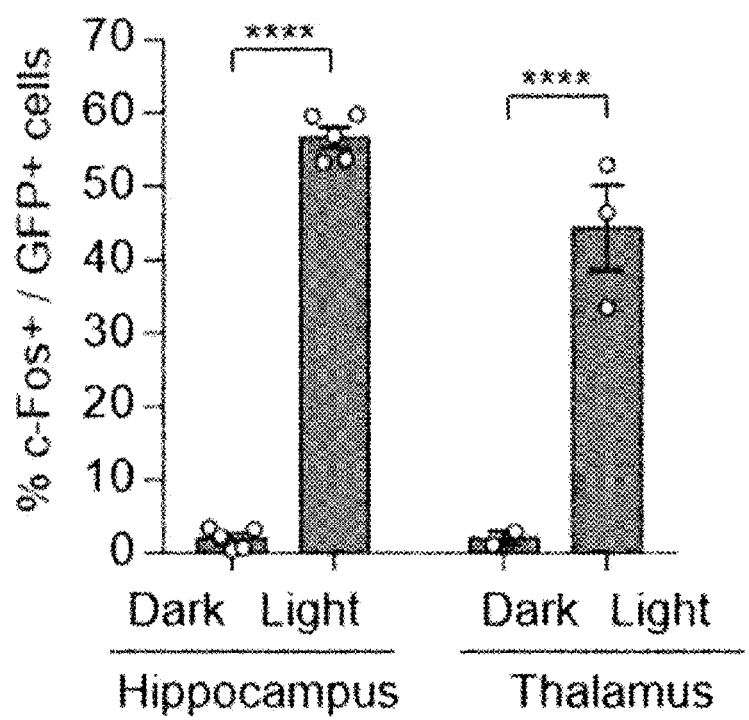
FIG. 15 is a graph showing the percentage of c-Fos-positive cells expressing monSTIM1 (P<0.0001; Sidak's tests).

In order to evaluate suitability of monSTIM1 as a deep brain modulator, c-Fos expression in monSTIM1 expressing astrocytes in hippocampus (HPC) and thalamus (TH) regions was examined. The results are shown in FIGS. 14 and 15. Referring to the results of FIGS. 14 and 15, 57% and 44% of the cell populations respectively expressing mon-STIM1 in the HPC and TH regions exhibited c-Fos expression by using the light stimulation, and accordingly, a $Ca^{2+}$ introduction and a downstream signal transmission were effectively induced through the non-invasive activation of monSTIM1.

Observation of Behavioral Characteristics

Finally, whether the induction of $Ca^{2+}$ signals through the non-invasive light transmission affects specific behaviors in awake mice was examined. In an anterior cingulate cortex (ACC), activity of voltage-dependent L-type $Ca^{2+}$ channels (Cav1.2, Cacna1c) was involved in social fear learning (e.g.: observational fear reaction). Mice having ACC-restricted deletion of Cav1.2 genes exhibited reduced observational fear due to impaired synaptic transmission or neuronal excitability However, a causal relationship between direct activation of the $Ca^{2+}$ signals and the observational fear was not tested. Accordingly, the present inventors used monSTIM1 or photo-insensitive OptoSTIM1 ($CRY2^{D387A}$) and targeted excitatory pyramidal neurons in ACC to examine socially transmitted fear responses.

Figure 16:
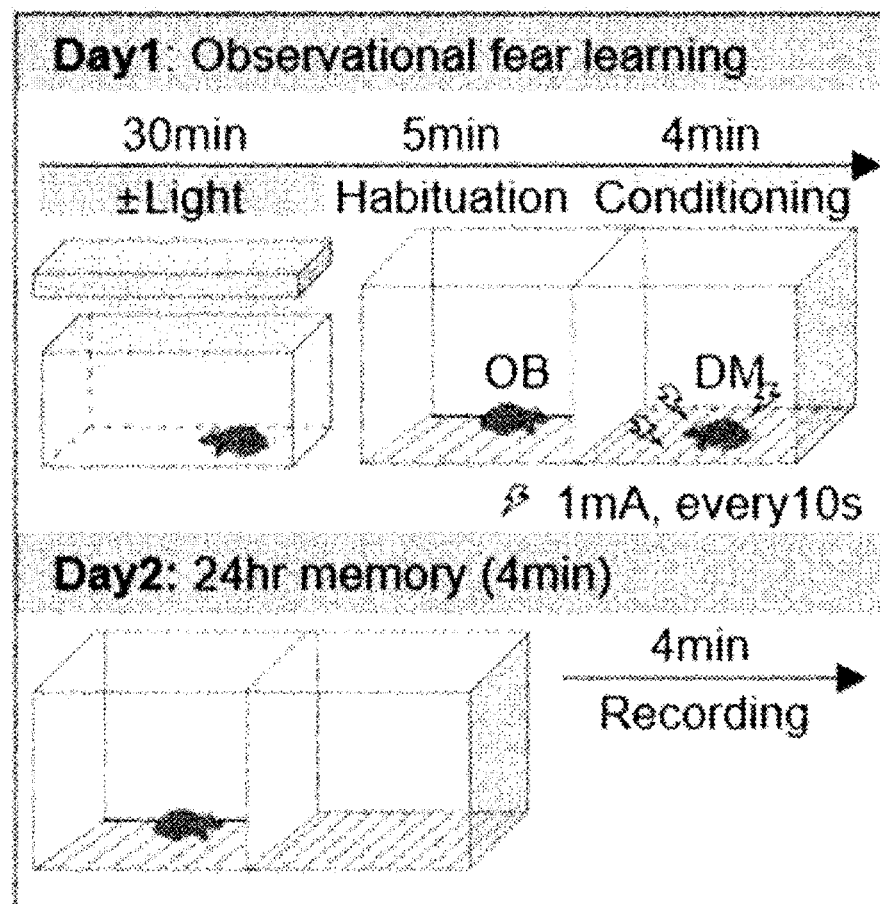
FIG. 16 is a schematic view for explaining the observational fear learning paradigm.

FIG. 16 is a schematic view for explaining the observational fear learning paradigm. In these experiments, observer mice alone were illuminated for 30 minutes in a home cage, and both the observer mice and demonstrator mice were moved into observational fear behavior chambers separated by a transparent plexiglass partition. The mice were habituated to a device for 5 minutes, but repetitive foot shocks were applied to demonstrator mice alone at 10 second intervals for 4 minutes in order to induce vicarious freezing responses of feelings and experiences in the observer mice.

In particular, the monSTIM1 activated mice showed significantly higher freezing levels during the training period (4 minutes).

Figure 17:
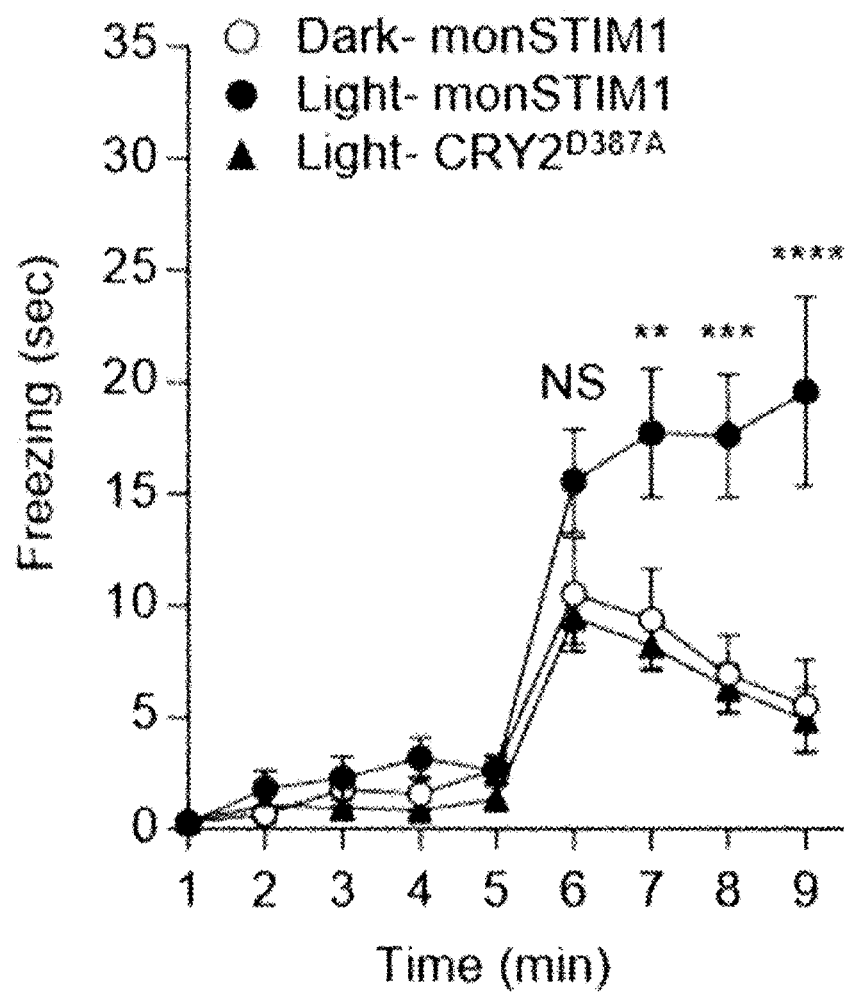
FIG. 17 is summary data showing the average time of freezing.
Figure 18:
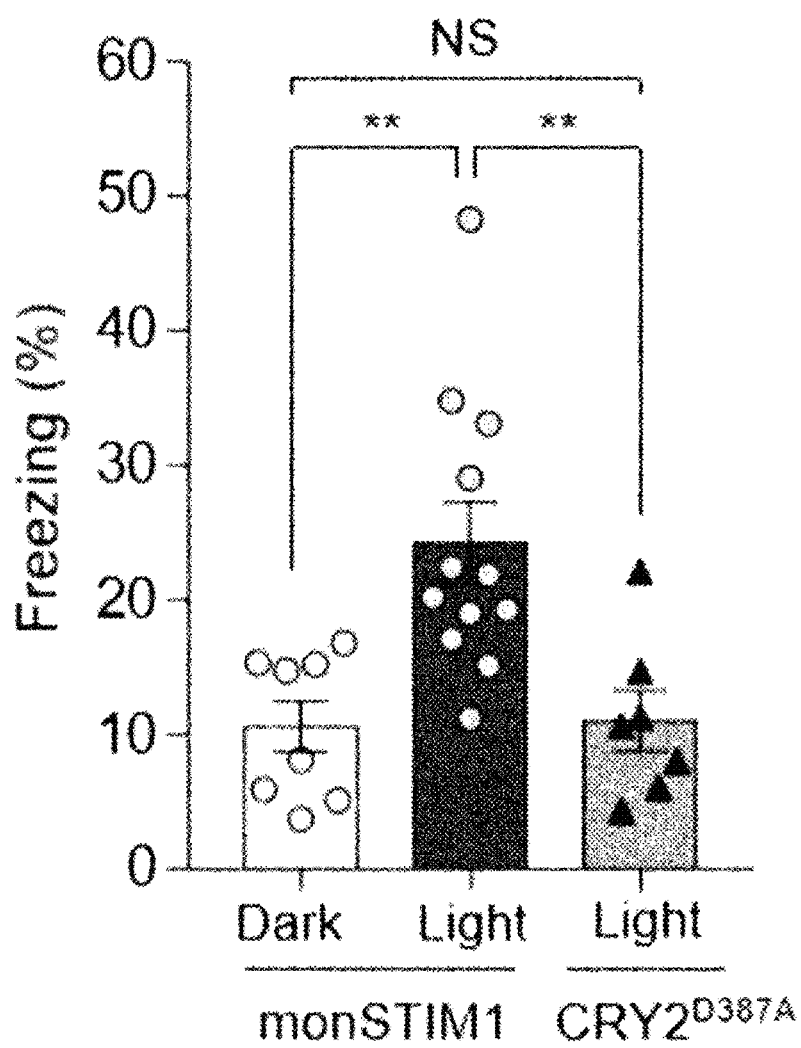
FIG. 18 is a graph showing the percentage of freezing time during a 24-hour memory test (P value is determined by Tukey's test).

After 24 hours, the data results of the observer mice exposed to the same conditioning chamber again are shown in FIGS. 17 and 18. Referring to the results of FIGS. 17 and 18, the observer mice exposed in the same conditioning chamber exhibited increased contextual fear memory compared with the control group mice, and accordingly, the $Ca^{2+}$ signals contributed to short-term and long-term social fear responses in ACC. Considering that the activation of monSTIM1 in ACC did not trigger motor skills or fear-like behaviors in the open field test, monSTIM1-mediated $Ca^{2+}$ induction in ACC selectively enhanced socially-transmitted fear response in the mice.

From these experiments, a $Ca^{2+}$ modulator to which the CRY2 variant was applied exhibited excellent photosensitivity and minimum changes of basal $[Ca^{2+}]$. Accordingly, monSTIM1 was sufficiently activated as a non-invasive light delivery system to induce subsequent $Ca^{2+}$ signal transmission in neurons and astrocytes in the brain region and thereby enabled regulation of specific brain functions and corresponding animal behaviors.

Although the experimental example has been described above, the scope of the invention is not limited thereto. The embodiments may be implemented in various ways within the scope of the detailed description of the invention and the accompanying drawings, and this also belongs to the scope of the invention.

INDUSTRIAL APPLICABILITY

It may be used in the field of non-invasive optogenetics technology for controlling cellular functions in vivo.

The invention claimed is:

1. A CRY2 variant in which
at least one of E279 and E281 having a negative charge among a $N_{277}SEGE_{281}$ sequence of SEQ ID NO: 1 is substituted with any one selected from the neutral amino acid group of alanine (A), isoleucine (I), leucine (L), valine (V), phenylalanine (F), methionine (M), and tryptophan (W), or
S278 or G280 in the $N_{277}SEGE_{281}$ sequence of SEQ ID NO: 1 is substituted with any one selected from a bulky amino acid group of tryptophan (W) and phenylalanine (F).

2. The CRY2 variant of claim 1, wherein the E281 is substituted with any one selected from the neutral amino acid group of alanine (A), isoleucine (I), leucine (L), valine (V), phenylalanine (F), methionine (M), and tryptophan (W).

3. The CRY2 variant of claim 1, wherein the neutral amino acid group is alanine (A).

4. The CRY2 variant of claim 1, wherein the substitution comprises E281A.

5. The CRY2 variant of claim 1, wherein a sequence consisting of at least 7 to 9 amino acids selected from the group of arginine (R), aspartic acid (D), proline (P), asparagine (N), alanine (A), and leucine (L) at the carboxy terminal of SEQ ID NO: 1 is inserted.

6. The CRY2 variant of claim 5, wherein the inserted sequence consists of a peptide of SEQ ID NO: 2 to SEQ ID NO: 16.

7. The CRY2 variant of claim 6, wherein E281 is substituted with any one selected from a neutral (or hydrophobic) amino acid group of alanine (A), isoleucine (I), leucine (L), valine (V), phenylalanine (F), methionine (M), and tryptophan (W).

8. The CRY2 variant of claim 6, wherein the neutral amino acid group is alanine (A).

9. The CRY2 variant of claim 6, wherein the substitution comprises E281A.

10. The CRY2 variant of claim 6, wherein the substitution is E281A and the inserted sequence is SEQ ID NO: 5 or 6.

11. A gene encoding the variant of claim 1.

12. An expression vector comprising the gene of claim 11.

13. A transfectant transfected with an expression vector of claim 12.

14. A $Ca^{2+}$ modulator comprising the CRY2 variant of claim 1 and an STIM1 protein bound to the N-terminus or C-terminus of the CRY2 variant.

* * * * *